(12) United States Patent
Badran et al.

(10) Patent No.: US 12,257,392 B1
(45) Date of Patent: *Mar. 25, 2025

(54) SYSTEMS AND METHODS FOR MEDITATION ENHANCEMENT

(71) Applicant: Bodhi NeuroTech, Inc., Charleston, SC (US)

(72) Inventors: Bashar Badran, San Ramon, CA (US); Baron Short, Charleston, SC (US)

(73) Assignee: Bodhi NeuroTech, Inc., Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,522

(22) Filed: Apr. 10, 2023

Related U.S. Application Data

(63) Continuation of application No. 16/639,189, filed as application No. PCT/US2018/045799 on Aug. 8, 2018, now Pat. No. 11,648,372.

(60) Provisional application No. 62/547,154, filed on Aug. 18, 2017.

(51) Int. Cl.
*A61M 21/02* (2006.01)
*A61N 1/04* (2006.01)
*A61N 1/20* (2006.01)
*A61N 1/36* (2006.01)

(52) U.S. Cl.
CPC ............ *A61M 21/02* (2013.01); *A61N 1/0476* (2013.01); *A61N 1/0496* (2013.01); *A61N 1/20* (2013.01); *A61N 1/36025* (2013.01); *A61N 1/0456* (2013.01); *A61N 1/36034* (2017.08)

(58) Field of Classification Search
CPC ... A61M 21/02; A61N 1/0476; A61N 1/0496; A61N 1/20; A61N 1/36025; A61N 1/0456; A61N 1/36034
See application file for complete search history.

(56) References Cited

U.S. PATENT DOCUMENTS

| 8,849,407 | B1 | 9/2014 | Danilov et al. |
| 8,909,345 | B1 | 12/2014 | Danilov et al. |
| 9,020,612 | B1 | 4/2015 | Danilov et al. |
| 9,044,606 | B2 * | 6/2015 | Harris ................. A61N 1/0456 |

(Continued)

OTHER PUBLICATIONS

A Double-Blind Study Exploring the Use of Transcranial Direct Current Stimulation (tDCS) to Potentially Enhance Mindfulness Meditation (E-Meditation) Brain Stimulation, vol. 10, Jan.-Feb. 2017, p. 1, col. 2.

(Continued)

*Primary Examiner* — Catherine M Voorhees
(74) *Attorney, Agent, or Firm* — Haynsworth Sinkler Boyd, P.A.

(57) ABSTRACT

A method for assisting a user with meditation includes applying, to the user, a distributor at or near a brain portion of the user; operating a signal generator to provide a signal to the brain portion the user, the signal being applied to the brain portion of the user by the distributor, and engaging in one or more meditation practices by the user while the signal is being applied to the brain portion of the user. The signal may correspond to an electrical signal, and the distributor may include an anode and a cathode. The anode may provide the signal to the user, and the cathode may receive the signal from the user to transfer the signal back to the signal generator.

14 Claims, 9 Drawing Sheets

(56) References Cited

U.S. PATENT DOCUMENTS

| | | |
|---|---|---|
| 9,597,504 B1 | 3/2017 | Danilov et al. |
| 9,656,069 B1 | 5/2017 | Danilov et al. |
| 9,656,078 B1 | 5/2017 | Danilov et al. |
| 11,648,372 B2* | 5/2023 | Badran ................ A61N 1/0496 600/26 |
| 2006/0173510 A1* | 8/2006 | Besio ..................... A61B 5/375 607/45 |
| 2009/0306741 A1 | 12/2009 | Hogle et al. |
| 2009/0312817 A1 | 12/2009 | Hogle et al. |
| 2011/0295096 A1* | 12/2011 | Bibian ................ A61B 5/7221 600/372 |
| 2014/0343625 A1* | 11/2014 | O Laighin ......... A61N 1/36034 607/48 |
| 2015/0005840 A1* | 1/2015 | Pal ..................... A61N 1/36025 607/45 |
| 2015/0290453 A1 | 10/2015 | Tyler et al. |
| 2015/0290454 A1 | 10/2015 | Tyler et al. |
| 2015/0375005 A1 | 12/2015 | Segal |
| 2017/0368329 A1* | 12/2017 | Tyler ...................... G10L 15/02 |
| 2018/0161626 A1* | 6/2018 | Fung ...................... G16H 40/63 |
| 2018/0296834 A1* | 10/2018 | John .................. A61N 1/36007 |
| 2020/0139112 A1* | 5/2020 | Aharonovitch ...... A61N 1/0476 |

OTHER PUBLICATIONS

PCT International Search Report, Nov. 30, 2018.
PCT Written Opinion of the International Searching Authority, Nov. 30, 2018.

* cited by examiner

SECTION A-A

SECTION B-B

SECTION C-C

SECTION D-D

SYSTEMS AND METHODS FOR MEDITATION ENHANCEMENT

BACKGROUND

This application claims priority to U.S. Nonprovisional patent application Ser. No. 16/639,189 filed on Feb. 14, 2020, which claims priority to International Application No. PCT/US2018/045799 filed on Aug. 8, 2018, which claims priority to U.S. Provisional Patent Application No. 62/547,154 filed on Aug. 18, 2017, the entire contents of the provisional application being incorporated herein by reference.

BACKGROUND

Meditation is a term that refers to a broad variety of practices that, when successfully completed, are generally known to provide many benefits to the person practicing meditation, including improvements to the person's mood (e.g. making the person calmer, more focused, more relaxed, happier, have an improved state of mind, less anxious, etc.) performance (e.g. athletic performance, occupational performance, etc.), addiction assistance (e.g. assist with overcoming substance abuse, etc.), sleep pattern assistance (e.g. the times of sleep, duration of sleep, etc.) enlightenment and/or general health and well-being. Meditation is difficult to learn and often requires extensive training, practice, and/or assistance. As a result, many of the individuals who would like to obtain the benefits of meditation are unable to do so because, for one reason or another, the individuals will not/are not able to invest the time, effort and/or resources to learn how to effectively meditate. Therefore, the benefits of meditation have largely been limited to those individuals who are able to invest the time, effort and/or resources to learn how to effectively meditate. There is a need for devices, systems methods, technologies and/or techniques that assist with the meditation process so that individuals are able to learn how to meditate and/or are able to enter a meditative state easier so that the benefits of meditation may be enjoyed by people who are not able to invest the time, energy and/or resources to effectively meditate using traditional methods.

SUMMARY

According to one possible implementation described herein, a method for assisting a user with meditation includes applying, to the user, a distributor at or near a brain portion of the user and operating a signal generator to provide a signal to the brain portion of the user by the distributor. The method further includes engaging in one or more meditation practices by the user while the signal is being applied to the brain portion of the user. The signal may be an electrical signal. The signal may be a direct current signal from about 5 volts to about 20 volts. The signal may have a current level from about 0.5 milliamps to about 5 milliamps, preferably from about 1 milliamp to about 2 milliamps. The distributor may include an anode and a cathode, the anode providing the signal to the user and the cathode receiving the signal from the user to transfer the signal back to the signal generator to complete a circuit. The anode may be placed at or near a right temple of the user, and the cathode may be placed approximately above a left eye of the user. The brain portion corresponds to an area of the user associated with one or more of: a frontal cortex of a brain of the user, a supplementary motor area of the brain, an auricular nerve, a cranial nerve, the left insula, the right insula, an olfactory nerve, an optic nerve, a trigeminal nerve, a facial nerve, a glossopharyngeal nerve, a vagus nerve, a hypoglossal nerve, or an auriculotemporal nerve. The distributor may include an area of contact at which the distributor is applied to the user, the distributor including a signal distributor at the area of contact. The signal distributor may be formed from hydrogel. The method may further include operating the signal generator to change the signal from a first signal to a second signal. The method may further include conducting an impedance test, by the signal generator, to determine whether a resistance of the user exceeds a threshold; and either applying the signal to the user if the resistance is below the threshold, or not applying the signal to the user if the resistance is above the threshold. The threshold may be from about 5,000 ohms to about 20,000 ohms. The method may further include cleansing an area of contact with the user when the resistance is above the threshold and conducting a second impedance test to determine whether the resistance is below the threshold.

According to another possible implementation described herein, a distributor configured to provide an electrical signal to a brain portion of a user to facilitate meditation includes an anode configured to apply the electrical signal to the user, the anode providing a first area of contact at which the electrical signal may be transferred to the user. The distributor further includes a cathode configured to receive the electrical signal from the user, the cathode providing a second area of contact at which the electrical signal may be received from the user. The distributor further includes a first electrical connector electrically connected to the anode, and a second electrical connector electrically connected to the cathode. The first area of contact may include a first signal disperser, and the second area of contact may include a second signal disperser. Both the first signal disperser and second signal disperser may correspond to a metallic array. The metallic array may be formed from silver trace or a conductive paint. The distributor may further include a first signal distributor formed from hydrogel on the first area of contact and a second signal distributor formed from hydrogel on the second area of contact. The distributor may further include a connecting section that connects the anode and the cathode, the connecting section configured to orient the anode at or near the right temple of the user when the cathode is oriented approximately over the left eye of the user.

According to another possible implementation described herein, a signal generator for providing a signal to a brain portion of a user to facilitate meditation includes a supply configured to provide the signal and a regulator connected to the supply. The regulator is configured to adjust the signal. The signal generator further includes one or more input devices configured to allow a user to control the signal. The signal generator further includes a signal connection connectable to a distributor to provide the signal to the brain portion of the user. A housing secures the supply, the regulator, the one or more input devices and the signal connection. The signal may correspond to an electrical signal, and the supply corresponds to a battery. The one or more input devices may include a first button corresponding to a first signal, a second button corresponding to a second signal, and a third button corresponding to a third signal. The first signal may correspond to a direct current electrical signal having a current of about 1 milliamp. The second signal may correspond to a direct current electrical signal having a current of about 1.5 milliamps. The third signal may correspond to a direct current electrical signal having a current of about 2 milliamps. The signal connection may include a first signal connection configured to provide the electrical signal to the distributor and a second signal connection configured to receive the electrical signal from the distributor. The signal generator may further include a processing unit that executes instructions to test an impedance of the user by providing an impedance signal to the distributor via the signal connection and determining whether the impedance associated with the user is above a threshold. The threshold may be from about 5,000 ohms to about 20,000 ohms, more particularly, about 10,000 ohms. The impedance signal may be different from the signal provided to the brain portion of the user to facilitate meditation and imperceptible to the user. Alternatively, the impedance signal may be the signal provided to the brain portion of the user to facilitate meditation. The signal generator may further include a display that provides a visual output to the user, the display connected to the housing.

In yet another implementation described herein, a system for facilitating meditation by providing a signal to a brain portion of the user includes a signal generator configured to provide the signal and a distributor connected to the signal generator, the distributor receiving the signal from the signal generator and applying the signal to the user. The signal generator may be connected to the distributor via a connector, the connector having a first end associated with the signal generator and a second end associated with the distributor. The signal may be an electrical signal in the form of direct current. The distributor may include an anode that provides the signal to the user and a cathode that receives the signal from the user. The anode may define a first contact area, and the cathode defines a second contact area. The first contact area may include a first signal disperser, and second contact area may include a second signal disperser. The first signal disperser and second signal disperser may be in the form of a metallic array. The first contact area may further include a first signal distributor, and the second contact area may further include a second signal distributor. The signal may corresponds to a current from about 0.5 milliamps to about 5 milliamps and a voltage from about 5 volts to about 40 volts.

DETAILED DESCRIPTION

Figure 1:
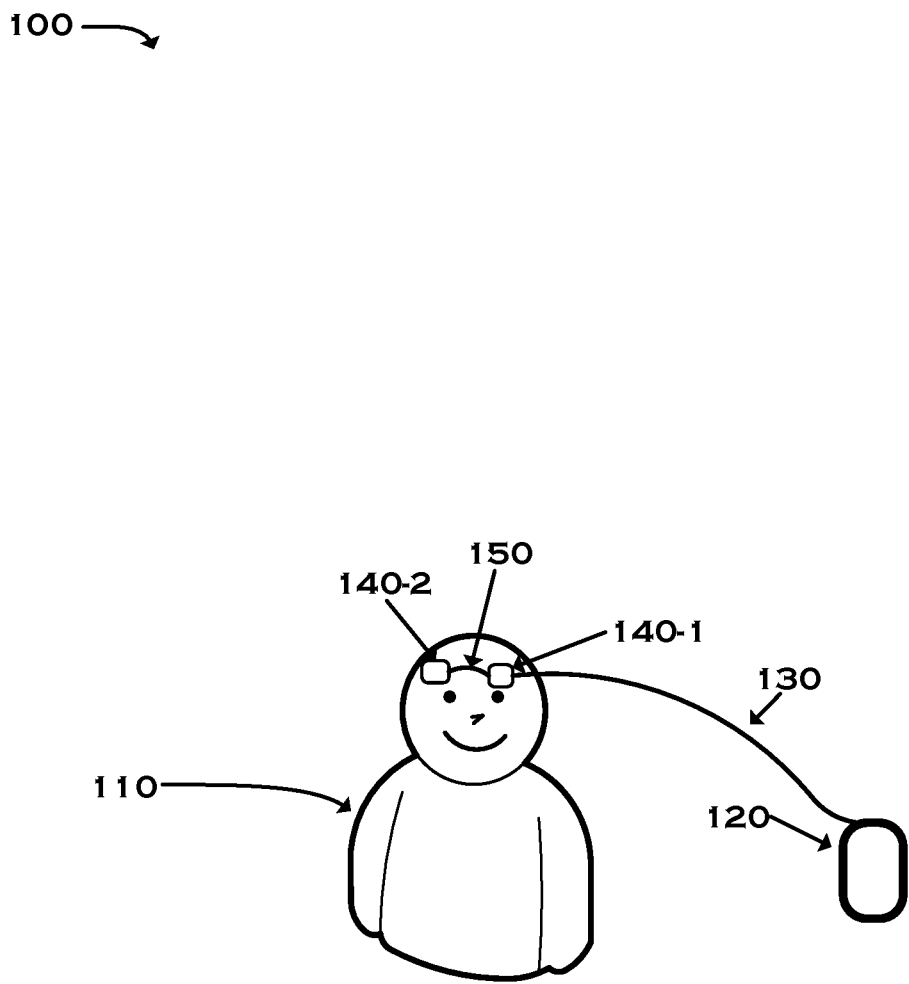
FIG. 1 illustrates a diagram of an example environment in which the systems, methods, technologies and/or techniques described herein may be implemented.

FIGS. 1-9 are attached hereto and incorporated herein by reference. The following detailed description refers to the accompanying FIGS. 1-9. The same reference numbers in different figures may identify the same or similar elements.

The devices, systems, methods, technologies and/or techniques (hereinafter, "systems and methods") described herein may assist users who wish to learn and/or practice meditation. Meditation refers to a broad range of established and novel practices that result in entering a "meditative state," which is generally associated with an enhanced mental state that is different from the typical states of human consciousness such as resting, sleeping, sitting, being active, etc. The enhanced mental state may be described as, for example, an enhanced state of focus, well-being, calm, detachment, bliss, insight, emptiness, a non-separate sense of self, altered consciousness, etc. Unlike traditional medical treatments, which provide benefits by directly treating symptoms, conditions, etc., the practice of meditation indirectly provides a variety of health benefits, including but not limited to mood improvement, cognitive benefits, athletic performance, addiction assistance, sleep, overall health, and enlightenment. The systems and methods may permit the user to more easily meditate by providing a signal to a portion of the brain, auricular nerves and/or cranial nerves via one or more distributors. The systems and methods may also, or alternatively, enhance meditation by adjusting the signal delivered to the user via the one or more distributors based upon the user's adjustment of a signal generator, instructions within the signal generator or another device and/or activity of the user's brain and/or cranial nerves. The systems and methods may provide meditation assistance to a single user and/or to two or more users in a group meditation system.

The systems and methods may provide a meditation enhancement system (hereinafter "meditation system") that may include a signal generator that may generate a signal (e.g. electrical signal (e.g. alternating current and/or direct current, etc.), ultrasonic sound wave signal, magnetic wave signal, a temperature change, etc. that is delivered to one or more distributors (e.g. electrodes, pads that distribute the input signal, transducer probes, static and/or dynamic magnets, a thermal/sensory apparatus, etc.) located at or near the brain (e.g. the left and/or right frontal lobe, the left and/or right temporal lobe, the supplementary motor area or SMA regions of the brain (including Pre-SMA, SMA, etc.), the cingulate cortex (including the posterior cingulate cortex, PCC), the left and/or right insula, auricular nerves, and/or cranial nerves (e.g. olfactory nerve, optic nerve, trigeminal nerve, facial nerve, glossopharyngeal nerve, vagus nerve (including auricular vagus nerve), hypoglossal nerve, auriculotemporal nerve, auricular nerves, etc.) (hereinafter the "brain portion"). The distributors may be placed on any surface of the body that may provide an input signal to the brain portion, including, but not limited to, the forehead, above the left and/or right eyebrow, the left and/or right temple, the supraorbital region, around the crown of the head (to engage the SMA or PCC regions of the brain), in or around the ears and/or other areas on or near the brain, auricular nerves, and/or cranial nerves, including areas having little and/or no hair. In one embodiment, the meditation system may include a distributor that includes an anode placed over the right eye near the right temple and a cathode placed on the left forehead above the eyebrow. The input signal may flow from the anode to the cathode to stimulate the brain portion. The distributors may additionally, or alternatively, monitor and/or record brain activity (e.g. using electroencephalography ("EEG"), other sensors, etc.).

The signal may be in the form of electrical power (e.g. direct current, alternating current, etc.), sound waves (including ultrasonic waves, etc), magnetic waves, thermal energy, tactile input, a combination of the foregoing, etc. The signal generator may automatically adjust the signal (e.g. based on instructions contained on a memory associated with signal generator, based on feedback from sensors associated with the signal generator, etc.), be manually adjusted (e.g. by the user, a meditation instructor, etc.), or be adjusted by a user device and/or by another device. Additionally, or alternatively, the signal generator may be controlled/automatically adjusted by a user device, based upon a meditation application (software instructions executed to control/automatically adjust the signal generator) and/or in response to information associated with the user (e.g. received from sensors monitoring brain activity, pulse rate, etc.). Adjusting the signal (e.g. increase or decrease the strength, the frequency, etc.) may enhance meditation and/or deliver a specific meditation experience. Adjusting the signal may also, or alternatively, include removing the signal and allowing the user to continue to meditate without the signal, which may promote unassisted meditation.

The signal generator may provide the same and/or different signals to two or more users. The signal generator may also, or alternatively, limit the input signal to prevent the input signal from harming (e.g. electrocuting, burning, etc.) the user. In one non-limiting embodiment, the signal generator may include a source that corresponds to a direct current power source in the form of a battery that delivers power to a source and/or a user at a voltage (e.g. from less than about one volt to about fifty volts, more particularly, 1.5 volts, 3 volts, 3.7 volts, 4.2 volts, 5 volts, 6 volts, 9 volts, 12 volts, 20 volts, etc.) and current (e.g., 01 mA, 1 mA, 2 mA, 5 mA, 10 mA, 20 mA, etc.) to the distributors. The voltage and/or current may be constant and/or may vary based upon user input, instructor input, and/or instructions contained in the signal generator, a user device and/or another device. The voltage and/or current may be adjusted by a regulator (e.g. increase/decrease voltage, current, frequency, etc.) and/or applied directly to the user without adjustment. In one embodiment, the voltage may be adjustable to overcome a resistance associated with a user (e.g. based on parameters such as skin resistance, thickness, moisture content, oil content, skull thickness, etc.) while the current remains a relatively constant. In another embodiment, the regulator may adjust the signal as needed by the user to engage in meditation (e.g. from a first signal, to a second signal, to a third signal, etc.). The signal generator may run a test to determine the level of resistance to the signal associated with the user and may apply the signal only if the test indicates that the resistance is acceptable. The signal generator may also, or alternatively, continuously monitor the resistance to the signal and may stop providing the signal if the resistance is above a threshold.

The distributors may include an adhesive and/or another substance to connect the distributors to the user and may further include a conducting agent (e.g. a hydrogel, a polymer hydrogel, a saline-based gel or liquid, etc.) that may transfer (e.g. equally distribute across an area, provide a current density (e.g., 01 mA/cm$^2$, .05 mA/cm$^2$, 1 mA/mc$^2$, 5 mA/cm$^2$, 10 mA/cm$^2$, etc.) to the user, etc.) the input signal to the user. The conducting agent may also, or alternatively, include one or more stimulants or biologically active substances (e.g. caffeine, etc.) that may be released to the user and that may further enhance meditation.

The meditation system may be used by a single user. Additionally, or alternatively, the meditation system may be administered to two or more users by one of the users and or by another person, such as a practitioner (e.g. a meditation instructor or teacher, etc.) and/or by a set of instructions (e.g. software instructions held in signal generator, a user device, another device connected to the signal generator and/or user device via a network, etc.), and/or guided by one or more of the two or more users. The meditation system may include meditation content, which may include audio content, video content, and/or virtual reality content. The meditation content may be provided directly by the signal generator, by a user device, etc. and/or indirectly by another device (e.g. headphones, a radio, a display, another device and/or through a virtual reality platform not included within the signal generator or user device, etc.).

The methods disclosed herein may include using the systems, methods, technologies and/or techniques disclosed herein to assist a user with meditation by providing a signal to a brain portion of the user. The systems and methods may further include adjusting the signal based upon information associated with the user obtained from a sensor located on the user, resistance associated with the user, and/or based upon instructions contained in a meditation application. The systems and methods may further include providing meditation content to the user to enhance meditation and/or further assist in the inducement of meditation.

FIG. 1 illustrates an example environment 100 in which the systems and methods described herein may be implemented. As shown in FIG. 1, environment 100 may include a user 110 (e.g. a meditator, or person would like to meditate, using the systems and methods herein), a signal generator 120, a connector 130, one or more distributors 140 (referred to collectively as "distributors 140" or individually as first distributor 140-1, second distributor 140-2, etc.), and/or a retainer 150. The components illustrated in FIG. 1 are provided for explanatory purposes only, and the systems and methods described herein are not limited to environment 100 or the components provided therein. There may be additional devices, components or systems; fewer devices, components or systems; different devices, components or systems; or differently arranged devices, components or systems than illustrated in FIG. 1. Also, in some implementations, one or more of the devices, components or systems of FIG. 1 may perform one or more functions described as being performed by another one or more of the devices, components or systems of FIG. 1.

Signal generator 120 may provide a signal to a distributor (e.g. first distributor 140-1, second distributor 140-2, etc.) and/or receive a signal back from a distributor via connector 130 as described herein. Signal generator 120 may provide, via connector 130, a signal that corresponds to electrical power (e.g. direct current, alternating current, etc.), sound waves (including ultrasonic waves, etc.), magnetic waves, thermal energy, tactile input, etc. to the one or more distributors. Signal generator 120 may provide a constant signal to a distributor via connector 130. For example, and not limitation, one example embodiment of signal generator 120 may provide a constant signal (i.e. an electrical signal varying only by about 10% in voltage and/or current for a period of time associated with a meditation and not adjustable by the user, etc.) in the form of a direct current electrical signal ("DC signal"). The DC signal may include a voltage that may be, for instance, about 2 volts to about 100 volts, preferably about 5 volts to about 40 volts, more preferably about 20 volts. The voltage used may be determined by a resistance associated with the user, a current level that will not harm the user, the amount of meditation assistance needed by the user, etc. The DC signal may include a current that may be, for instance, from 0.01 milliamps ("mA") to 10 mA, preferably 0.1 mA to 5 mA, more preferably 0.5 mA to 2 mA. The current and/or voltage may be relatively constant and/or may vary based upon the treatment delivered, information associated with the user, etc. Signal generator 120 may have different settings that correspond to different signals. Additionally, or alternatively, signal generator 120 may have a setting that corresponds to providing a signal that varies between an upper threshold and a lower threshold at a constant frequency (e.g., .01 hertz, .5 hertz, 1 hertz, 5 hertz, 60 hertz, 120 hertz, etc.). For example, and not limitation, one example embodiment of signal generator 120 may produce a DC signal that varies (e.g. a linear change, a sinusoid, any other rate of change, etc.) between a low threshold of 3 volts to a high threshold of 20 volts and/or from a low threshold of 1 mA to a high threshold of 2 mA at a frequency.

Alternatively, signal generator 120 may be adjustable to modify the signal (i.e. increase the strength of the signal, the frequency of the signal, etc.) delivered to the user. For instance, a user and/or an instructor may manually adjust (e.g. using controller as described herein, etc.) signal generator 120 to modify the signal. Additionally or alternatively, signal generator 120 may automatically adjust the signal based upon executing instructions contained on a memory associated with signal generator and/or based upon instructions received from another device (e.g. a user device, etc.). Additionally, or alternatively, signal generator 120 may execute and/or receive instructions to modify the signal in response to inputs (e.g. from sensors associated with the user, etc.) as will be discussed in greater detail later herein. Adjusting the signal may enhance meditation and/or provide two meditators with the same and/or similar meditation experiences. The signal generator may provide the input signal to one or more users. The signal generator may also, or alternatively, include safety mechanisms (e.g., fuses, limit switches, etc.) to limit the strength of the signal to prevent the signal from harming (e.g. electrocuting, burning, etc.) the user. The signal generator may also, or alternatively, execute instructions to perform a test sequence that may monitor a characteristic of the user and/or signal to determine whether the signal may be applied to a user. The test sequence may include, for example, an impedance test to determine the resistance to the signal when the distributors are applied to the user, when the resistance of the user is below a threshold associated with successful signal delivery, etc. Additionally, or alternatively, the signal generator may continuously monitor a characteristic of the user and/or signal to determine whether a threshold has been crossed and may stop providing the signal if such threshold has been exceeded.

Connector 130 may connect two or more of the signal generator 120 and distributors 140 described herein, and other devices and/or components described later herein to transfer the signal from the signal generator to the distributors 140, to receive the signal back from the distributors, to allow the signal generator to receive information from a sensor, etc. For example, and not as limitation, connector 130 may receive the signal from the signal generator 120 and deliver the signal to the one or more distributors 140 so that the signal may be applied to the user 110. Additionally, or alternatively, connector 130 may receive the signal from one or more distributors 140 after the signal has been applied to the user 110 and deliver it back to signal generator 120, such as to complete a circuit.

As shown in FIG. 1, one embodiment of connector 130 may have a first end associated with one or more distributors 140 and a second end associated with the signal generator 120. Additionally, or alternatively, connector 130 may have a first end associated with a first distributor and a second end associated with a second distributor. Additionally, or alternatively, connector 130 may have a first end associated with a signal generator, a second end associated with a first distributor 140-1 and a third end associated with a third distributor 140-2. Connector 130 may be formed from a material or materials that may transfer a signal (e.g. conductive materials such as copper, etc., found in electrical wire, etc.), permit communication (e.g. electronic communication of data, etc.), and may include insulation (e.g. sheathing, etc.) that may prevent discharge of the signal along connector 130 anywhere other than through connector's 130 connections with distributors 140 and/or signal generator 120. Connector 130 may connect to signal generator 120 and/or distributors via known connection styles (e.g. electrical connectors (e.g. snap lug connectors, barrel plug connectors, quick connectors, etc.), USB, splicing, etc.). While distributors 140 are shown connected to signal generator 120 via connector 130, signal generator 120 may be directly connected to/formed as a part of one or more distributors 140, which may eliminate the need for connector 130.

Distributors 140 may connect to connector 130 and/or signal generator 120 to receive a signal. Distributor may transfer the signal to the user and/or receive a signal that has been transferred to a user via another distributor 140 (e.g. to complete a circuit by sending the signal back to signal generator 120, etc.). Distributor 140 may correspond to one or more connections to a user which may be used to transfer a signal to the user. Distributor 140 may include a single connection, two connections (i.e. a first distributor and a second distributor), three connections, etc. In an example embodiment having two connections, first distributor may apply the signal to the user, and second distributor may receive the signal that has been applied to the user. For example, first distributor 140-1 may receive a signal from signal generator 120 and apply the signal to a brain portion of user 110. The brain portion may be a portion of the brain, auricular region and/or cranial nerves of user 110 (e.g. the left and/or right frontal lobe, the left and/or right temporal lobe, the SMA and PCC regions of the brain, the left and/or right insula, olfactory nerve, optic nerve, trigeminal nerve, facial nerve, glossopharyngeal nerve, vagus nerve (including auricular vagus nerve), hypoglossal nerve, auriculotemporal nerve, auricular nerves, etc.). A second distributor 140-2 may receive the signal after it has been applied to the brain portion. In the example embodiment depicted in FIG. 1, the signal may be applied to user 110 from the first distributor 140-1, i.e. acting as an anode if applying electrical current, and may be applied to the user and received by the second distributor 140-2, which may act as a cathode. In this arrangement, the locations of first distributor 140-1 and second distributor 140-2 may determine the brain portion to which the signal is applied (i.e. in, around and/or between first distributor 140-1 and second distributor 140-

2). As shown in FIG. 1, the first distributor 140-1 may be placed over the right temple, and the second distributor 140-2 may be placed on the left side of the forehead above the eyebrow. However, the location of distributors 140 is not so limited. Distributors 140 may be placed in any location that may be used to apply the signal to the desired brain portion of the user 110, including, for instance, the forehead, above the left and/or right eyebrow, the left and/or right temple, the supraorbital region, around the crown of the head, in and/or around the ears, and/or other areas on or near the brain, auricular nerves and/or cranial nerves, especially those areas with little and/or no hair (as too much hair may limit and/or preclude signal from being transferred to brain portion in some instances). While FIG. 1 depicts two distributors 140, a user may apply less (e.g. 1 distributor) or more (e.g. 3, 4, 5, 6 or more distributors, etc.) in order to apply one or more signals to one or more brain portions.

Distributors 140 may be formed from a material or materials that may be conductive in order to transfer signal to user 110 and/or receive signal that has been applied to the user. For example, distributors 140 may include a conductive material (e.g., saline solution, single-layer conductive polymer hydrogel, multiple-layer conductive polymer hydrogel, etc.) that is used to transfer the signal to/from the user. The conductive materials used to form distributors 140 may be uniformly conductive which may spread the signal to the user at a uniform signal density (e.g. a current density of 0.01 mA/cm$^2$ to 5 mA/cm$^2$, etc.) that may correspond to a safe level at which the signal may be applied (e.g. without burning, electrocuting, etc.) to the user. Distributors 140 may also include insulation, which may prevent the signal from being discharged anywhere other than where intended. Distributors 140 may additionally, or alternatively, include adhesives on a surface of the distributors 140. The adhesive may maintain distributors 140 on a specific location on the user. Distributors 140 may be any size or shape. The surface of distributor 140 that is applied to the user may be sized to direct the signal to a specific brain portion (e.g. sized to fit on a specific location on the head) and/or to apply the signal at a signal density. For example, and not limitation, distributors 140 may range from 5 cm$^2$ to 65 cm$^2$, preferably 10 cm$^2$ to 40 cm$^2$, more preferably 12 cm$^2$ to 25 cm$^2$. Distributors 140 may include conventional connectors to connect distributors 140 to signal generator 120 and/or connector 130. Distributors 140 may also include one or more biologically active substances (e.g. stimulants, such as caffeine, etc.) that may be released to user (e.g. when the distributor 140 is applied to user, when a signal is applied to distributor, etc.) to further enhance meditation.

Retainer 150 may be a head garment, strap, visor, a clip, a headband, or other similar device that may maintain one or more distributors 140 on a user and/or determine the distance between a first distributor 140-1 and second distributor 140-2. Additionally, or alternatively, retainer 150 may connect to one or more distributors 140 to transfer the signal to/from the distributor 140 to/from the signal generator 120 and/or the connector 130. As shown in FIG. 1, retainer 150 may maintain first distributor 140-1 and second distributor 140-2 on user 110 and may transfer the signal that has been applied to user 110 and received by second distributor 140-2 to connector 130, such as via electrical or other connections on retainer, to be transferred back to signal generator 120.

Figure 2:
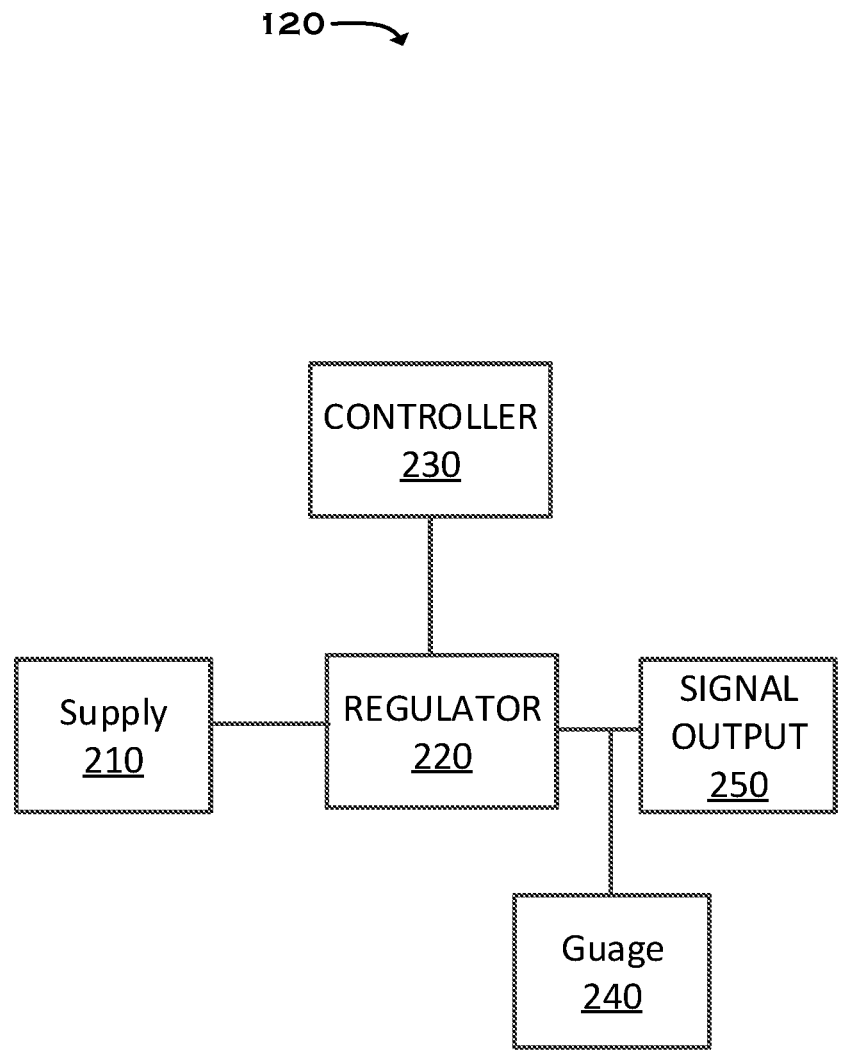
FIG. 2 illustrates a diagram of example components that may correspond to the signal generator of FIG. 1.

FIG. 2 illustrates a diagram of the signal generator 120 of FIG. 1. As shown in FIG. 2, signal generator 120 may include a supply 210, a regulator 220, a controller 230, a gauge 240 and a signal output 250. The components of signal generator 120 may be connected in a way that allows them to communicate and/or distribute power, energy, a signal, etc. between the components. The devices, components and systems illustrated in FIG. 2 are provided for explanatory purposes only, and signal generator 120 is not intended to be limited to the devices, components, or systems provided therein. There may be additional devices, components or systems; fewer devices, components or systems; different devices, components or systems; or differently arranged devices, components or systems than illustrated in FIG. 2. For example, while signal generator 120 is depicted as including a controller 230, a regulator 220 and a gauge 240, signal generator 120 may not include one or more of these elements. Also, in some implementations, one or more of the devices, components or systems of FIG. 2 may perform one or more functions described as being performed by another one or more of the devices, components or systems of FIG. 2.

Supply 210 may correspond to a source for the energy used to generate the signal. For example, and not as limitation, supply 210 may correspond to a source for electrical power (e.g. direct current, alternating current, etc.), sound waves, magnetic waves, thermal energy, tactile input, etc. to the one or more distributors. In an example embodiment, supply 210 may correspond to a source for electrical power and may be formed from one or more conventional batteries (e.g. a 1.2, 1.5, 3, 3.7, 4.2, 4.5, 5, 6, 9, 12, 24 etc. volt battery) and/or may be a connection to a source of power (e.g. a conventional electrical outlet, such as a 110 volt US outlet). In another example embodiment, source may correspond to power delivered from a user device (e.g. from the battery of a user device, from a connection, such as a USB connection, of the user device through which power may be transmitted, etc.). In another example embodiment, source may correspond to kinetic energy device (e.g. a manual crank, bike, etc. that converts kinetic energy into, for instance, electric energy, etc.).

Regulator 220 may receive energy from supply 210 and may transform (e.g. increase/decrease voltage, current, frequency, amplitude, etc.) the energy into a signal. Regulator 220 may include conventional regulating equipment, such as an inverter (to convert direct current into alternating current), a converter (alternating current to direct current), a voltage reducer/transformer (to reduce/increase voltage), a current regulator (to increase/decrease the current), an amplifier (to modify sound waves), etc. Additionally, or alternatively, the energy from supply 210 may be the signal. For example, and not limitation, regulator 220 may include a transformer to change the voltage delivered from supply 210 in order to provide a signal at an increased voltage (e.g. higher than the source voltage) that will allow the signal to overcome resistance associated with a user (e.g. based on conditions of the user, such as skin thickness, moisture content, hair, skull thickness, etc.), a decreased voltage (e.g. for more comfort, etc.) and/or allow a signal to be delivered at a current (e.g. a lower current than would be delivered at a lower voltage, a constant current, etc.).

Controller 230 may be operated by a user, another meditator, a meditation instructor, etc. or receive an input from the signal generator (i.e. a the signal generator may execute instructions to operate controller 230, as further described herein), and/or another device, such as a user device/another device (via a network as further described herein), to adjust the signal via the regulator 220. Additionally, or alternatively, signal generator and/or other devices may communicate directly with regulator 220 to adjust the signal. Controller 230 may be in any form (e.g. a dial, buttons, touch screen, other input devices, etc.) that may be used to provide information to regulator 220 to adjust signal (e.g. increase/decrease voltage, current, frequency, amplitude, etc.).

Gauge 240 may measure the signal and provide information associated with the signal (e.g. amplitude, frequency, voltage, current level, temperature, sound level, etc.) to a conventional gauge display (e.g. a liquid crystal display screen, an analog gauge, a display panel, etc.). The gauge display may be part of gauge 240 and may be located on signal generator 120. Additionally, or alternatively, gauge 240 may send the information associated with the signal to another device.

Signal output 250 may correspond to a connection point (e.g. a plug, a socket, a nomex connector, a male and/or female fitting, a splice, etc.) that may connect signal generator 120 to connector 130 and/or distributors 140 to allow signal to be transferred from the signal generator 120 to a user and/or received back to the signal generator 120 from the user.

Figure 3:
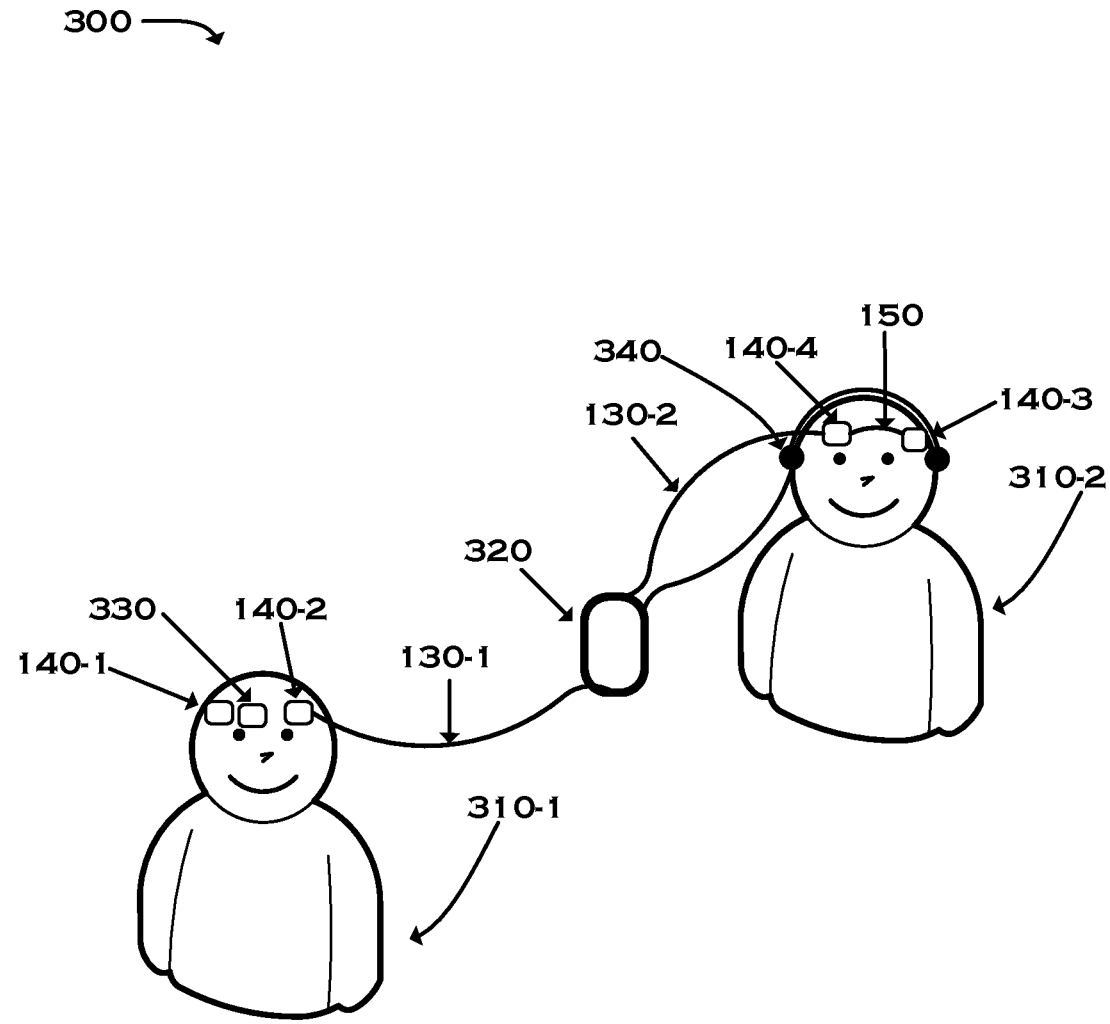
FIG. 3 illustrates an example environment in which the systems, methods, technologies and/or techniques described herein may be implemented.

FIG. 3 illustrates an alternative example environment 300 in which the systems and methods described herein may be implemented. As shown in FIG. 3, environment 300 may include a first user 310-1 associated with a signal generator 320 via a first connector 130-1 and a second user 310-2 associated with the signal generator 320 via a second connector 130-2. First user 310-1 and second user 310-2 both meditate using the systems and methods described herein. First user 310-1 may be operably connected to a first distributor 140-1, a second distributor 140-2 and a sensor 330. For example, and not limitation, the first distributor 140-1, second distributor 140-2 and sensor 330 may be connected to first user 310-1 with adhesive. Second user 310-2 may be operably connected to headphones 340, a third distributor 140-3 and a fourth distributor 140-4. The third distributor 140-3 and fourth distributor 140-4 may be secured to second user 310-2 via retainer 150. The devices, components and systems illustrated in FIG. 3 are provided for explanatory purposes only, and environment 300 is not intended to be limited to the devices, components, or systems provided therein. There may be additional devices, components or systems; fewer devices, components or systems; different devices, components or systems; or differently arranged devices, components or systems than illustrated in FIG. 3. Also, in some implementations, one or more of the devices, components or systems of FIG. 3 may perform one or more functions described as being performed by another one or more of the devices, components or systems of FIG. 3.

The first distributor 140-1, second distributor 140-2, third distributor 140-3, and fourth distributor 140-4 may function that same as or similar to the first distributor 140-1 and second distributor 140-2 of FIG. 1. Additionally, or alternatively, retainer 150 may function the same as, or similar to, retainer 150 of FIG. 1. Additionally, or alternatively, the second connector 130-2 may function the same as, or similar to, the connector 130 of FIG. 1. First connector 130-1 may function that same as, or similar to, connector 130 of FIG. 1 except that first connector 130-1 is connected to sensor 330 in addition to first distributor 140-1, second distributor 140-2, and signal generator 320. In this configuration, first connector 130-1 may provide information from sensor 330 to signal generator 320 as further described herein.

Signal generator 320 may function similar to signal generator 120 of FIGS. 1 and 2 except that, for instance, signal generator 320 may provide a signal to first user 310-1 and to second user 310-2. The signal provided by signal generator 320 to first user 310-1 may be the same as and/or different from the signal provided by signal generator 320 to second user 310-2. While signal generator 320 is depicted as providing a signal to two users, signal generator 320 may provide a signal to a single user and/or more than two (e.g. 3, 4, 5, 6 or more, etc.) users.

Signal generator 320 may receive information associated with first user 310-1 from sensor 330 via first connector 130-1 and may process the information associated with first user 310-1 to adjust signal (i.e. signal delivered to first user 310-1 and/or second user 310-2) based upon the information associated with first user 310-1. Signal generator 320 may adjust the signal based upon instructions contained on a memory associated with signal generator 320 as further described herein. Signal generator 320 may store, install and/or execute an application (e.g., a mobile application, logic, software application installed on a user device, server, etc.) that enables the signal generator 320 to provide a signal, to modify a signal, to receive and process information associated with a user, and/or to provide audio and/or video content as further described herein.

Figure 5:
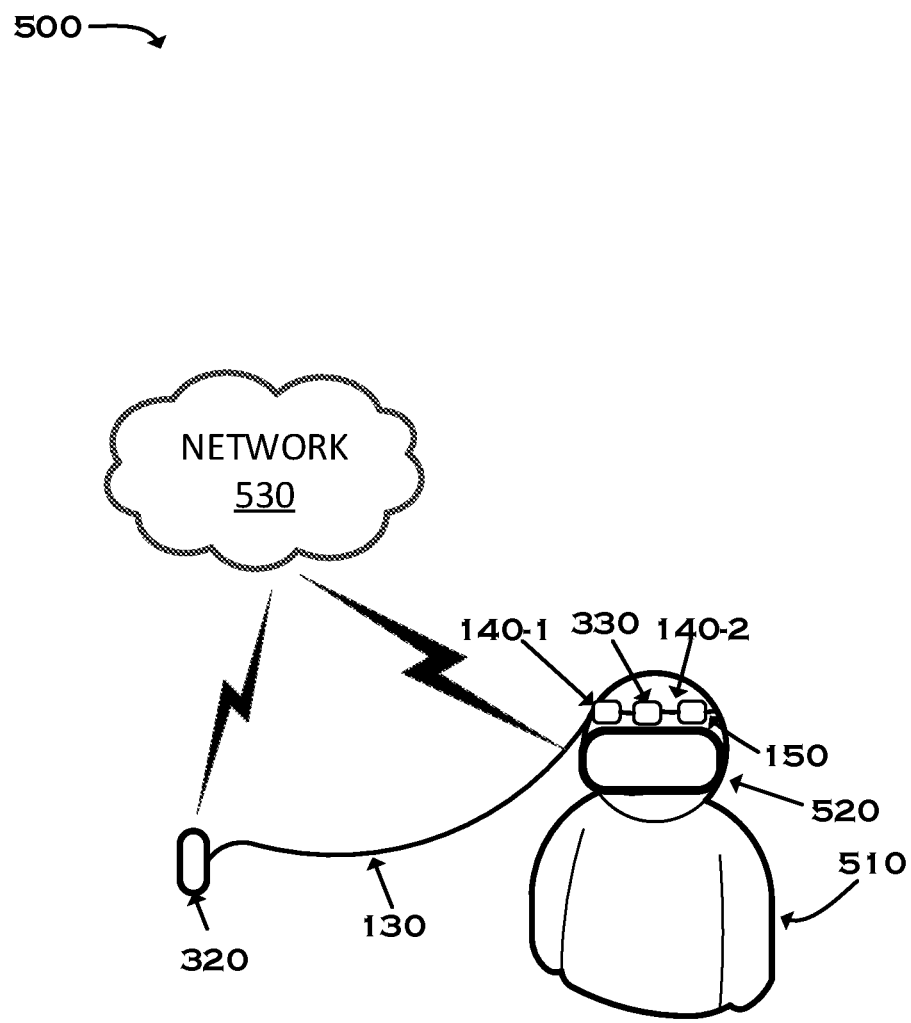
FIG. 5 illustrates an example environment in which the systems, methods, technologies and/or techniques described herein may be implemented.

Sensor 330 may monitor the first user 310-1 to obtain information associated with the first user 310-1 and provide (e.g. via connector 130-2, directly to signal generator 320 via a direct connection and/or a wireless connection, etc.) information associated the first user 310-1 to the signal generator and/or a user device or other device as further described with respect to FIG. 5. Information associated with the first user 310-1 may include, for instance, conditions associated with a brain portion (e.g. brain waves, etc.) as well as other biological information associated with the first user 310-1 (e.g. heart rate, blood pressure, temperature, etc.). Sensor may be any type of traditional sensor for measuring biometric activity, including electroencephalography sensors, electrocardiogram sensors, heart rate sensors, transducers, etc. Sensor 330 may be separate from and/or formed as a part of distributors 140. While sensor 330 is depicted on user 310-1's forehead, sensor 330 may be on any location of a user (e.g. arm cuffs, fingertip sensors, chest-mounted sensors, etc.).

Sensor 330 may provide information associated the first user 310-1 to signal generator 320. Signal generator 320 may process the information associated with the first user 310-1 and may transmit (e.g. via gauges, a display on signal generator 320 or anther device, via headphones, etc.) the information associated with the first user 310-1 to the first user 310-1, the second user 310-2 and/or some other person or device. Additionally, or alternatively, signal generator 320 may execute instructions to modify the signal delivered to first user 310-1 and/or second user 310-2 based upon the information associated with the first user 310-1. While sensor 330 is depicted as a single sensor on first user 310-1, there may be multiple sensors on each user. Signal generator 320 may execute instructions to modify a signal delivered to a user based upon information associated with the user obtained from one or more sensors associated with the user. Additionally, or alternatively, signal generator 320 may store information associated with a user on memory included within signal generator 320 (or another device) and may execute instructions to modify the signal based upon a comparison of the stored information associated with a user with the signal delivered to the user at the time.

Headphones 340 may be standard headphones (e.g. headphones, ear buds, etc.) and/or any other known device that may deliver audio content to second user 310-2. Additionally, or alternatively, audio content may be delivered to one or more users via a speaker, which may be part of the signal generator 320, a user device, and/or another device. While headphones 340 are shown on second user 310-2, first user 310-1 and/or any other person may obtain audio content via headphones 340. The audio content may include a variety of meditation content including, for example, training instructions to assist the user when meditating (e.g. recorded meditation sessions conducted by a meditation instructor or practitioner), calming music, soothing sounds, binaural beats, etc. The audio content may be provided to headphones 340 by signal generator 320, by a user device associated with signal generator 320 and/or by another device via a network as will be described later. The audio content may be modified based upon information associated with the user obtained from sensor 330. The same audio content may be delivered to multiple users at the same time to provide a group meditation experience. Additionally, or alternatively, different audio content may be delivered to different users based upon, for instance, each user's preference, the user's brain waves/biological state as measured by a sensor, etc. In addition to audio content, the systems and methods herein provide that video content may be delivered through a display associated with the signal generator 320, a user device and/or another device. The video content may facilitate meditation (e.g. instructions on meditation provided by, for instance, an instructor or practitioner, background for optimum meditation setting, such as calming relaxation videos, nature scenes, etc.).

Figure 4:
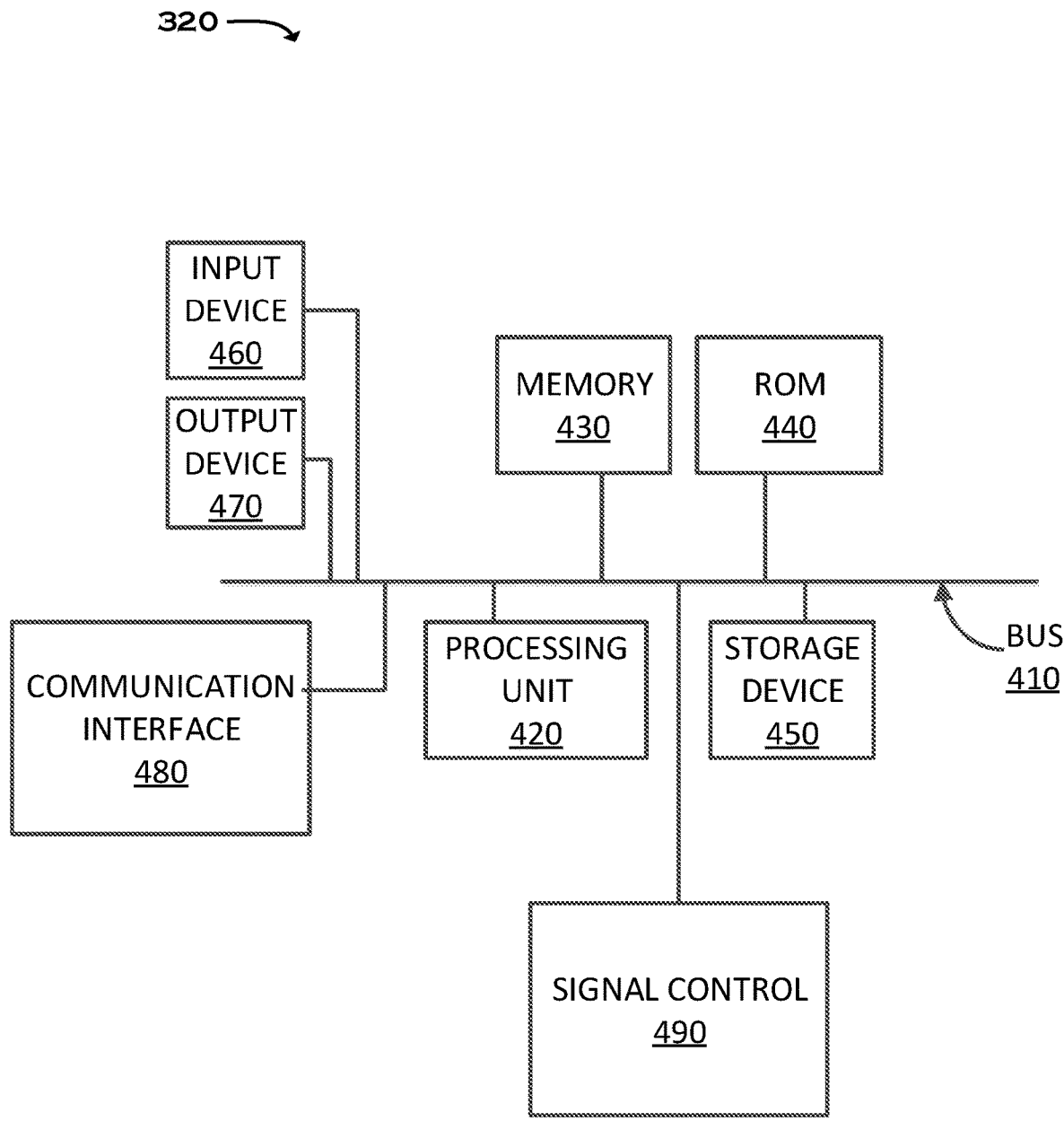
FIG. 4 illustrates a diagram of example components of the signal generator of FIG. 3.

FIG. 4 illustrates a diagram of example components of signal generator 320 of FIG. 3. Additionally, signal generator 320 may contain one or more of the components of signal generator 120 depicted in FIG. 2, such as a supply, regulator, etc. Signal generator 320 may include bus 410, processing unit 420, memory 430, ROM 440, storage device 450, input device 460, output device 470, communication interface 480 and/or signal control 490. Bus 410 may include a path that permits communication among the components of signal generator 320 depicted in FIG. 4. In other implementations, signal generator 320 may include fewer components, additional components, different components, or differently arranged components than illustrated in FIG. 4. For example, signal generator 320 may include a user device (as described later herein). In still other implementations, one or more components of signal generator 320 may perform one or more tasks described as being performed by one or more other components of signal generator 320.

Processing unit 420 may include a processor, multiple processors, microprocessors, or other types of processing logic that may interpret, execute, and/or otherwise process information and/or data contained in, for example, the storage device 450 and/or memory 430. The information may include computer-executable instructions and/or data that may implement one or more embodiments of the systems and methods. Processing unit 420 may comprise a variety of hardware. The hardware may include, for example, some combination of one or more processors, microprocessors, field programmable gate arrays (FPGAs), application specific instruction set processors (ASIPs), application specific integrated circuits (ASICs), complex programmable logic devices (CPLDs), graphics processing units (GPUs), or other types of processing logic that may interpret, execute, manipulate, and/or otherwise process the information. Processing unit 420 may comprise a single core or multiple cores. Moreover, processing unit 420 may comprise a system-on-chip (SoC) or system-in-package (SiP). Additionally, or alternatively, processing unit 420 (and/or another component of signal generator 320) may be configured to generate and/or update keys (e.g., encryption keys, rotating keys, etc.).

Memory 430 may include a random access memory (RAM) or another type of dynamic storage device that may store information (e.g. information associated with a user, meditation schedules, instructions, programs, etc.) and instructions for execution by processing unit 420. ROM 440 may include a ROM device or another type of static storage device that may store static information and/or instructions for use by processing unit 420. Storage device 450 may include a magnetic and/or optical recording medium and its corresponding drive. In some implementations, memory 430 or storage device 450 may also be implemented as solid state memory, such as flash-based memory.

Input device 460 may include a mechanism that permits a user, instructor and/or one of the components of environment 300 (e.g. signal information from distributors, information associated with a user from sensors 330, etc.) to input information to signal generator 320, such as a keyboard, a mouse, a pen, a button, a single or multi-point touch interface, an accelerometer, a gyroscope, a microphone, voice recognition and/or biometric mechanisms, etc. Output device 470 may include a mechanism that outputs information to the operator, including a display, a speaker, jack for headphones 340, etc. In the case of a display, the display may be a touch screen display that acts as both an input and an output device. Input device 460 and/or output device 470 may be haptic type devices, such as joysticks or other devices based on touch.

Communication interface 480 may include any transceiver-like mechanism that enables signal generator 320 to communicate with other devices (e.g. sensors, distributors, user devices, other signal generators, etc.) and/or systems. For example, communication interface 480 may include mechanisms for communicating with another device or system via a network (e.g. a local area network, the internet based on, for example, an Internet version 6 (IPv6) protocol, an Hypertext Transfer Protocal (HTTP), a secure HTTP protocol (HTTPS), a tunneling protocol, etc. and/or via wired or wireless link (e.g., a Bluetooth protocol, a near-field protocol, beaming, etc.)), e.g., a network interface card.

Signal generator 320 may perform certain operations in response to processing unit 420 executing software instructions contained in a computer-readable medium, such as main memory 430. For instance, signal generator 320 may implement a meditation application by executing software instructions (e.g. a meditation application including signal instructions based upon information associated with the user, video content, audio content, etc.) from main memory 430. A computer-readable medium may be defined as a non-transitory memory device, where the memory device may include a number of physically distributed memory devices. The software instructions may be read into main memory 430 from another computer-readable medium, such as storage device 450, or from another device via communication interface 480. The software instructions contained in main memory 430 may cause processing unit 420 to perform processes described herein as being performed by signal generator (e.g. adjusting the signal, etc.). Alternatively, hardwired circuitry may be used in place of, or in combination with, software instructions to implement processes described herein. Thus, implementations described herein are not limited to any specific combination of hardware circuitry and software.

Signal control 490 may perform the functions of controller 230 (modify a signal, such as by converter, inverter, etc.) and/or regulator 220 (convert energy from source to a signal) of FIG. 2. Signal control 490 may modify signal manually, similar to controller 230 of FIG. 2. Additionally, or alternatively, signal control 490 may be controlled automatically by signal generator 320 based upon instructions contained on signal generator 320 and/or received by signal generator 320.

FIG. 5 illustrates an alternative example environment 500 in which the systems and methods described herein may be implemented. As shown in FIG. 5, environment 500 may include a user 510 operably connected to a first distributor 140-1, a second distributor 140-2, a sensor 330 via retainer 150, and a signal generator 320, which may be operably connected to the first distributor 140-1 second distributor 140-2 and sensor 330 via connector 130. The user 510 may additionally, or alternatively, be operably connected to a user device 520 which may communicate with the signal generator 320 via a network 530 as further described herein. The devices, components, networks, and systems illustrated in FIG. 5 are provided for explanatory purposes only, and environment 500 is not intended to be limited to the devices, components, or systems provided therein. There may be additional devices, components or systems; fewer devices, components or systems; different devices, components or systems; or differently arranged devices, components or systems than illustrated in FIG. 5. Also, in some implementations, one or more of the devices, components or systems of FIG. 5 may perform one or more functions described as being performed by another one or more of the devices, components or systems of FIG. 5.

The connector 130, first distributor 140-1, second distributor 140-2, signal generator 320, sensor 330, and retainer 150 may function the same and/or similar to the similarly named components described above with respect to FIGS. 1 & 3. In addition, one or more of signal generator 320, sensor 330, first distributor 140-1 and/or second distributor 140-2 may communicate with user device 520 via network 530.

User device 520 may include any computation and communication device capable of providing audio, visual and/or virtual reality content and/or communicating via a network 530. For example, user device 520 may include a tablet computer, a personal communications system (PCS) terminal (e.g., such as a smart phone that may include data processing and data communications capabilities), a personal gaming system, a virtual reality system, a combination of the foregoing and/or another type of computation or communication device. Additionally, or alternatively, user device 520 may include logic, such as one or more processing or storage devices, that can perform processing activities on behalf of a user, signal generator 320 and/or another one or more of the components and/or devices described herein.

User device 520 may be configured to perform communication operations by sending data to and/or receiving data via network 530 from one or more of signal generator 320, sensor 330, distributors 140, and/or another device (e.g. another user device, another signal generator, sensor, etc.). Data may refer to any type of machine-readable information having substantially any format that may be adapted for use in one or more networks and/or with one or more components. Data may include digital information or analog information. Data may further be packetized and/or non-packetized. User device 520 may include logic for performing computations on user device 520 and may include the components illustrated in FIG. 4 in an example implementation. Such components may execute one or more instructions to perform functions as described herein. In one non-limiting implementation, the user device 520 may not be in persistent communication and/or connection with network 530 but may, when accessed and/or communicated with, communicate with signal generator 320, sensor 330, another user device 520, and/or another device.

User device 520 may store and/or execute a meditation application to enable the user device 520 to communicate with the signal generator 320, one or more distributors 140 and/or sensors 330 to obtain and/or monitor information associated with the user 510 and/or information associated with the signal. Additionally, or alternatively, the meditation application may communicate with signal generator 320 to provide meditation instructions, which may include instructing the signal generator 320 on the strength, frequency, and/or another parameter of the signal to be delivered to user 510. The meditation instructions may be based upon instructions stored on a memory associated with user device and may, for example, adjust the signal based upon information received from sensor 330, a distributor 140, etc. In one non-limiting example embodiment, user device 520 may include a signal generator. For example, and not limitation, user device 520 may process information associated with the user 510 received from sensor 330 and may communicate with signal generator 320 to adjust the signal delivered to the user 510. Additionally, or alternatively, user device 520 may communicate with a user device associated with another user and/or another person (e.g. meditation instructor, etc.) to send information associated with the user 510, to adjust the signal delivered to the user 510, etc. Additionally, user device 520 may provide audio, video and/or virtual reality content to the user 510 and/or may modify the audio, video and/or virtual reality content delivered to the user 510 based upon instructions contained in the meditation application, information received from sensor 330, signal generator 320, another user device, etc. Virtual reality content may, for example, simulate a group meditation session in which the user may view other virtual meditators, virtual instructors, etc. A virtual meditation session may replicate a one-on-one and/or group meditation session.

Network 530 may include one or more wired and/or wireless networks. For example, network 530 may include a wide area network (WAN) a metropolitan network (MAN), a telephone network (e.g. the Public Switched Telephone (PSTN)), an ad hoc network, an intranet, the Internet, a fiber optic based network, and/or a combination of these or other types of networks. Additionally, or alternatively, network 530 may include a cellular network, a public land mobile network (PLMN), a second generation (2G) network, a third generation (3G) network, a fourth generation (4G) network (e.g., a long term evolution (LTE) network), a fifth generation (5G) network, and/or another network. The devices, components and/or systems, described herein, may communicate via network 530 to provide assistance with meditation pursuant the systems and methods described herein. While FIG. 5 depicts user device 520 communicating with signal generator 320 via a wireless network, all of the devices herein may communicate via wired and/or wireless networks. For example, and not limitation, connector 130 and/or an additional connector (not shown) may connect user device 520 to first connector 140-1, second connector 140-2, sensor 330 and/or signal generator.

FIGS. 6A-6E illustrate a non-limiting example embodiment of a distributor 600 that may be used in connection with the systems and/or methods described herein. Distributor 600 may include a first layer 601, a second layer 602, an anode 610, a cathode 620, a connecting section 630, signal carriers 640, and a signal connection section 650. The components illustrated in FIGS. 6A-6E are provided for explanatory purposes only, and the disclosure herein is not intended to be limited to the components reflected in the drawings. There may be additional components, fewer components, different components, or differently arranged components than illustrated in FIGS. 6A-6E. Also, in some implementations, one or more of the components of the distributor 600 may perform one or more functions described as being performed by another one or more of the components of distributor 600. For example, and not limitation, anode 610 and cathode 620 are described herein as providing the signal to the user and receiving the signal that has been applied to the user, respectively. Alternatively (and depending on how the distributor is connected to a user device) anode 610 may serve as cathode 620 and vice versa. Further, the signal may cause anode 610 to serve as cathode 620 and vice versa (e.g. alternating current signals, reversing the flow of the signal via the signal generator, etc.). Additionally, or alternatively, while electrical connectors 651 and 652 are illustrated as residing at a single signal connection section 650, electrical connectors 651 and 652 may be split, with one residing near the anode 610 and the other residing near the cathode 620, or at any other location(s) on distributor 600.

Distributor 600 may provide an electrical signal (e.g. AC signal or DC signal) to a user via anode 610 and cathode 620 using the systems and/or methods described herein. Distributor 600 may include a first layer 601 that may correspond to a layer of material that may form a base for distributor 600. First layer 601 may be formed from a material or materials of sufficient strength and toughness to support the static and/or dynamic loads (e.g., forces, torques, tensions, compressions, stresses, strains, etc.) imparted to distributor 600 by the user (e.g. applying distributor 600 to user, removing distributor 600 from user, twisting distributor 600, etc.). Further, first layer may be formed from a material that is an electrical insulator (e.g. polymers, plastics (polyethylene terephthalate, polypropylene, PVC, etc.), Teflon, other known insulators, etc.) to limit and/or prevent the signal from passing through first layer 601. While first layer 601 is shown as being formed from a single piece of material, first layer 601 may be composed of one or more pieces of material. The types and shapes of first layer 601 are not intended to be limited to those shown in FIGS. 6A-6E.

First layer may serve as a base for the conducting elements (e.g. signal dispersers 660, signal distributors 670, signal carriers 640, electrical connectors 651 and 652, etc.) of distributor 600. For example, as shown in the embodiment reflected in FIGS. 6A-6E, first layer 601 forms a part of anode 610, cathode 620, connecting section 630 and signal connection section 650.

Distributor 600 may also include second layer 602. Second layer 602 may, like first layer 601, be an electrical insulator. Additionally, or alternatively, second layer 602 may provide a textured surface to some or all of distributor 600. Second layer 602 may be formed from a material or materials of sufficient strength and toughness to support the static and/or dynamic loads (e.g., forces, torques, tensions, compressions, stresses, strains, etc.) imparted to distributor 600 by the user (e.g. applying distributor 600 to user, removing distributor 600 from user, twisting distributor 600, etc.). Further, second layer 602 may be formed from a material that is an electrical insulator (e.g. polymers, plastics (polyethylene terephthalate, polypropylene, PVC, etc.), Teflon, combinations of insulators, other known insulators, etc.) to limit and/or prevent the signal from passing through second layer 602. Second layer 602 may also, or alternatively, include a textured surface. While second layer 602 is shown as being formed from a single piece of material, second layer 602 may be composed of one or more pieces of material. The types and shapes of second layer 602 are not intended to be limited to those shown in FIGS. 6A-6E.

Figure 6A:
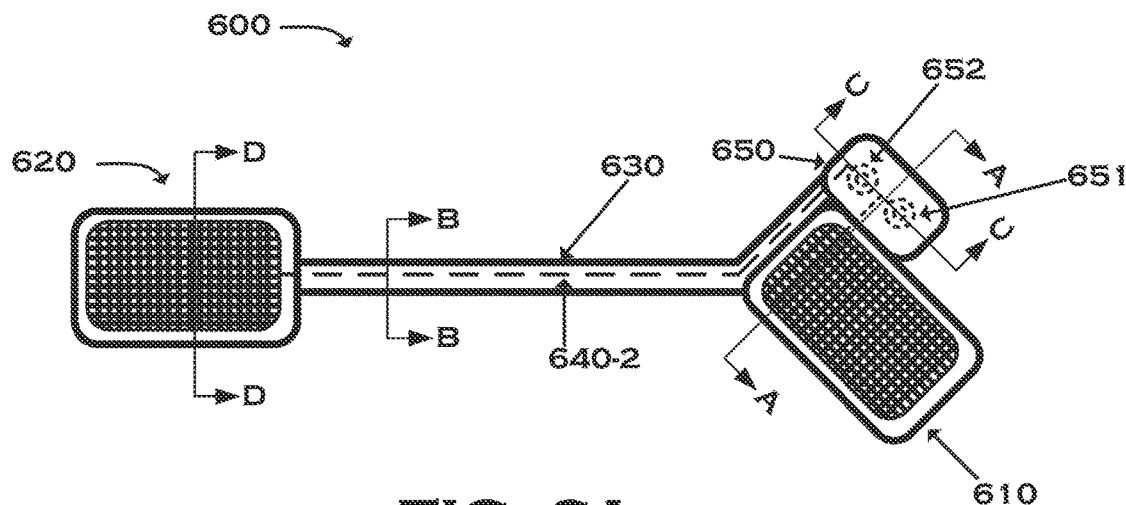
FIGS. 6A through 6E illustrate a non-limited example embodiment of a distributor that may be used in connection with the systems, methods, technologies and/or techniques described herein.
Figure 6B:
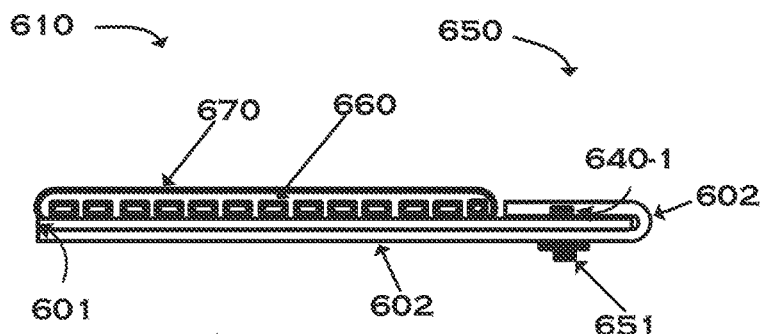
Figure 6C:
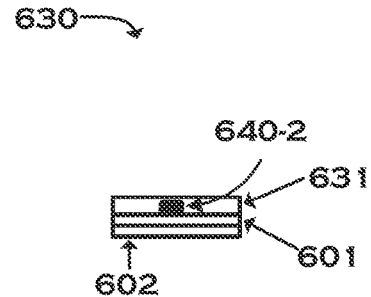

Anode 610 may provide the user with a signal using the systems and/or methods described herein. As shown in FIG. 6B, anode 610 may include first layer 601, second layer 602, signal disperser 660 and signal distributor 670. The components associated with anode 610 in the Figures are provided for explanatory purposes only, and the disclosure herein is not intended to be limited to, or to require, the components reflected in the drawings. There may be additional components, fewer components, different components, or differently arranged components than illustrated in FIGS. 6A-6E. Also, in some implementations, one or more of the components of anode 610 may perform one or more functions described as being performed by another one or more of the components of anode 610 (e.g. a layer may be removed, signal disperser and/or distributor may be combined, have one removed, etc.).

Anode 610 may receive a signal (e.g. a signal that has been provided to distributor from, for instance, a signal generator) that is to be applied to a user and apply the signal to the user at an area of contact. The signal may be applied to the user by signal disperser 660 and/or signal distributor 670. Signal disperser 660 may correspond to an area of conductive material that approximately defines the area of contact between the anode and the user and through which signal is distributed when signal is delivered to user. Ideally, the signal is evenly dispersed across the area of signal disperser 660. As shown in FIGS. 6A, 6B and 6E, signal disperser 660 may correspond to metallic array (e.g. a grid of metal wires or other solid metallic components, a grid formed from silver print, electrically conductive paint, or similar conductive material which may be applied to first layer, etc.) that receives the signal from signal carrier 640-1 and disperses the signal across the area of signal distributor 660. The area of signal distributor 660 is ideally approximately equivalent to the area of contact with user when distributor 600 is applied to user. Dispersing the signal across the area of signal disperser 660 may make applying the signal to the user safer and/or more comfortable for the user (i.e. may prevent injury or burns by spreading the signal across the area, prevent or reduce signal spikes, etc.). The area of signal disperser 660 may be determined by the signal delivered to the user (i.e. the amounts of voltage and/or current, etc.) to ensure that the signal is comfortable/not harmful yet still sufficient to stimulate meditation. The area of signal disperser 660 may determine the size of anode 610 and/or cathode 620, which may have about the same area of contact with the user. Signal disperser 660 may be placed between first layer 601 and signal distributor 670 (if signal distributor 670 is used/is separate from signal disperser 660). In some instances, signal disperser 660 is applied directly to the user, such as when signal distributor 670 is not included in distributor 600. In those embodiments, a user may apply a conducting material (e.g. ultrasound gel, saline solution, oils, jellies, creams, etc.) between distributor 600 and the user to make applying the signal safer and/or more comfortable.

Signal distributor 670 may correspond to a conducting agent that receives the signal from signal disperser 660 and distributes the signal across an area of contact with the user. Alternatively, signal distributor 670 may receive the signal from signal carrier 640 and may distribute the signal across the area of contact with the user, which may eliminate the need for signal disperser 660. Signal distributor 670 may be located between signal distributor 660 and the user when the distributor is applied to the user (i.e. covering the signal distributor). Signal distributor 670 may be formed from a material or materials that are electrically conductive and that may be used to comfortably (i.e. distributing the signal across the area of signal distributor 670) apply a signal to the user. For example, and not limitation, signal distributor may be formed from hydrogel (e.g. such those hydrogel products sold by R&D medical products), polymer gels, a saline gel, etc. Additionally, signal distributor 670 may be a material that serves as an adhesive to temporarily bond anode 610 and/or cathode 620 to a user, which may connect distributor 600 to the user to allow the user to meditate using the systems and/or methods described herein. In this embodiment, a user may apply the anode 610 to a brain portion by simply placing signal distributor 670 at the desired location and allowing the adhesive of signal distributor 670 to hold the anode 610 in the desired location. Signal distributor 670 may receive the signal from signal disperser 660 and may spread the signal across the area of contact with the user, which may further make the delivering the signal safer and/or more comfortable to the user.

Cathode 620 may receive the signal that was provided to the user via anode 610 and may route the signal back to electrical connector 652 (e.g. via signal carrier 640-2). As shown in FIG. 6E (and the similarities with 6B), cathode 620 may be formed from the same and/or similar components as anode 610 (and may serve as anode 610 when, for instance, the signal is received by distributor 600 at electrical connector 652). For example, cathode 620 may include first layer 601, second layer 602, signal disperser 660 and signal distributor 670. The components associated with cathode 620 in the Figures are provided for explanatory purposes only, and the disclosure herein is not intended to be limited to, or to require, the components reflected in the drawings. There may be additional components, fewer components, different components, or differently arranged components than illustrated in FIGS. 6A-6E. Also, in some implementations, one or more of the components of cathode 620 may perform one or more functions described as being performed by another one or more of the components of cathode 620 (e.g. a layer may be removed, signal disperser and/or distributor may be combined, have one removed, etc.).

Cathode 620 may receive the signal that was applied to the user via anode 610 and may deliver the signal back to electrical connector 652 via signal carrier 640-2. Cathode 620 may define an area of contact with the user that may be equal to the area associated with the signal disperser 660 and/or signal distributor 670 of the cathode. In some embodiments, cathode 620 may serve as anode 610 when the connector associated with electrical connector 652 carries the signal to distributor 600.

Connecting section 630 may correspond to section of distributor 600 that connects anode 610 and cathode 620 and/or cathode 620 (or anode 610) to signal connection section 650. Connecting section 630 may be any size and shape. As shown in FIG. 6A, connecting section 630 may help orient anode 610 and cathode 620 by setting the distance between the two. Additionally, or alternatively, connecting section 630 may orient anode 610 and cathode 620 for placement on a target area of a user. For example, in the embodiment depicted in FIG. 6A through 6E, when anode 610 is placed roughly at or around the right temple (e.g. not on hair line, roughly between right eye and right ear), connecting section 630 may orient cathode 620 such that it may be placed over the left eye or at some area on the forehead roughly over the left eye. This orientation is depicted in FIG. 7C. Connecting section 630 may be formed in any size and/or shape to connect and/or orient the components of distributor 600, including, but not limited to, the orientation of FIG. 7B and any other orientations needed to allow the anode and/or cathode to provide a signal to the brain portions described herein.

Connecting section 630 may also, or alternatively, include a signal carrier 640 which may transfer the signal between components of distributor 600. For example, in the embodiment depicted in FIGS. 6A and 6C, connecting section 630 may include signal carrier 640-2, which may carry the signal between cathode 620 and electrical connector 652. Connecting section 630 may be formed from first layer 601 and/or second layer 602, which may also form part of anode 610, cathode 620 and connecting section 650. Additionally, or alternatively, connector 630 may include third layer 631. Third layer 631 may insulate signal carrier 640-2 by partially surrounding signal carrier 640-2. Insulating signal carrier 640-2 may prevent signal from being disrupted (e.g. due to an arc, short, etc.). Third layer 631 may be formed the same or similar materials as first layer 601 and/or second layer 602. Additionally, or alternatively, third layer 631 may correspond to a paint, sealant and/or coating that has insulating properties.

Figure 6D:
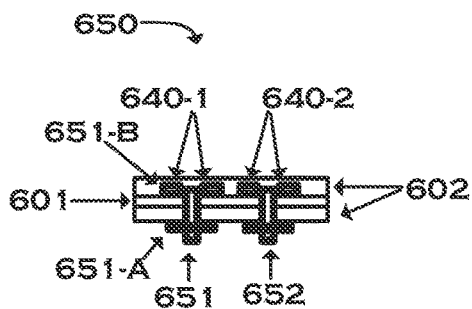
Figure 6E:
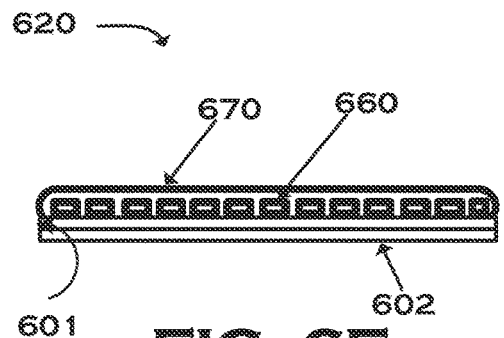

As shown in FIGS. 6A, 6B and 6D, signal connection section 650 may be one or more areas of distributor 600 that includes one or more electrical connectors, such as electrical connectors 651 and 652. While the embodiment depicted in FIGS. 6A, 6B and 6D reflect a single signal connection section 650 that includes both electrical connectors 651 and 652, there may be separate signal connection sections for each electrical connector. As shown in FIG. 6D, signal connection section 650 may be formed from first layer 601 and/or second layer 602. In the embodiment depicted herein, second layer 602 may, as shown in FIG. 6B, wrap around first layer 601 to reside on both sides of first layer 601. As shown in FIG. 6D, this configuration may allow second layer to insulate electrical connectors 651 and 652 and signal carriers 640-1 and 640-2. This method of insulating components may also, or alternatively, be used on other areas of distributor 600, such as connecting section 630. Electrical connectors 651 and 652 may be electrically connected to anode 610 and cathode 620, respectively. For example, electrical connectors 651 may have a first end which may connect to an electrical connector (such as an electrical connector of connector 130 or a connection with signal generator) to receive an electrical signal from signal generator and a second end which may connect to signal carrier 640 (e.g. signal carrier 640-1) to provide the signal to anode 610. Electrical connector 652 may have a third end which may connect to cathode 620 (e.g. via signal carrier 640-2) to receive the signal from cathode 620 and a fourth end which may connect to an electrical connector (such as an electrical connector of connector 130, a connection with signal generator, etc.) to provide the signal to signal generator. As depicted in FIG. 6D, electrical connector 651 has a first end 651-A that connects with a standard electrical connector, such as quick connector, a snap, a plug, etc., and a second end 651-2 that is located opposite first layer 601 from first end 651-A. Second end 651-B may contact signal carrier 640-1 to transfer the signal from the electrical connector 651 to anode 610 via signal carrier 640-1. Similarly, electrical connector 652 may have a first end associated with an electrical connector and a second end, opposite the first layer from first end, associated with signal carrier 640-2.

In the embodiment depicted herein, signal carriers 640 and signal emitters 660 may be formed from an electrically conductive material that may be directly applied (e.g. painted, soldered, etc.) to first layer 601 for ease of manufacture. For example, signal carriers 640 and signal emitters 660 may be formed from an electrically conductive coating (e.g. silver trace, PCB trace, nickel-based paints, etc.) that may be applied to first layer 601 to create the conductive paths of distributor 600. Alternatively, the conductive paths herein may be formed from other conductive materials, such as copper wire, solid conductive materials, etc.

Figure 7A:
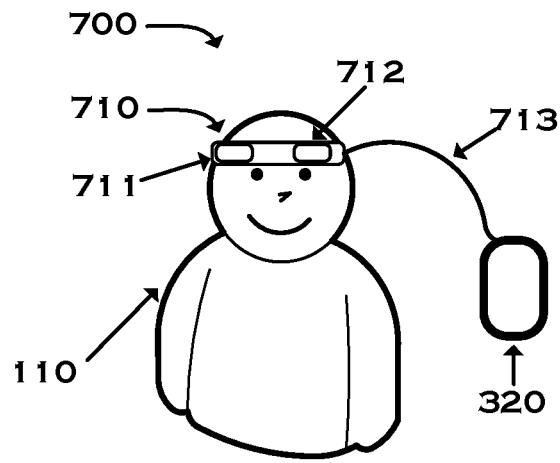
FIGS. 7A through 7C illustrate alternative example environments in which the systems, methods, technologies and/or techniques may be implemented.
Figure 7B:
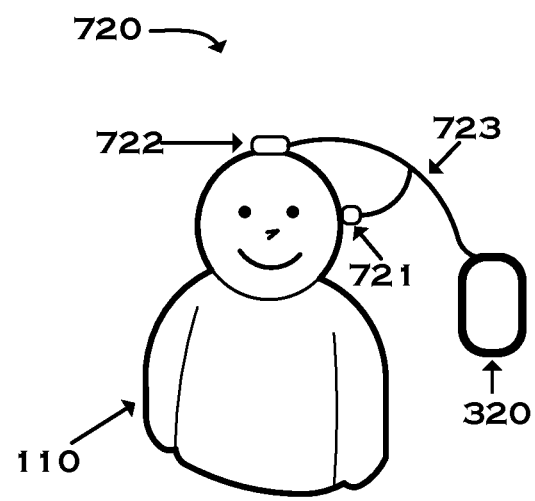
Figure 7C:
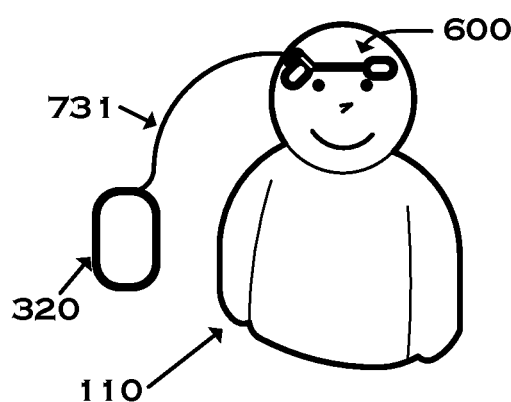

FIGS. 7A through 7C depict alternative non-limiting environments in which the systems and/or methods described herein may be implemented. As shown in FIG. 7A, environment 700 may include a user 110 who may be wearing a headband 710 that includes a first distributor 711 (e.g. an anode, etc.) and second distributor 712 (e.g. a cathode, etc.). The headband 700 may apply the first distributor 711 and/or second distributor 712 to the user and retain them in place on the user. Additionally, the headband 700 may partially or completely cover the distributors 711 and 712. Headband 710 may be connected to a signal generator, such as signal generator 320, via connector 713. While signal generator 320 is depicted as being separate from headband 700, headband 700 may include a signal generator on or inside of headband 700, which may provide an all-in-one arrangement (i.e. all components are on headband) that allows the user to practice the systems and methods described herein.

FIG. 7B illustrates an alternative non-limiting environment in which the systems and/or methods may be provided to a user. As shown in FIG. 7B, environment 720 may include a user who may be connected to a first distributor 721 and a second distributor 722 which are connected to a signal generator, such as signal generator 320, via connector 723. First distributor 721 may be located at or near an auricular region of the user 110, and second distributor 722 may be located at or near a supplementary motor area of the user 110. First distributor 721 and/or second distributor 722 may connect to signal generator 320, such as via connector 723, to allow a signal to be delivered to a user to facilitate meditation using the systems and/or methods described herein.

FIG. 7C illustrates another non-limiting environment in which the systems and/or methods may be provided to a user. As shown in FIG. 7C, environment 730 may include a user 110 who has applied distributor 600 to a brain portion, the distributor being connected to a signal generator, such as signal generator 320, via connector 731. As discussed with regard to FIGS. 6A-6E, distributor 600 is applied to a brain portion of user, and the connecting section of distributor 600 may help orient the anode and cathode of the distributor 600 such that the anode is placed near the right temple and the cathode is placed approximately above the left eye. Distributor 600 may receive a signal from signal generator 320 via connector 731 to provide the signal to the user 110.

Figure 8:
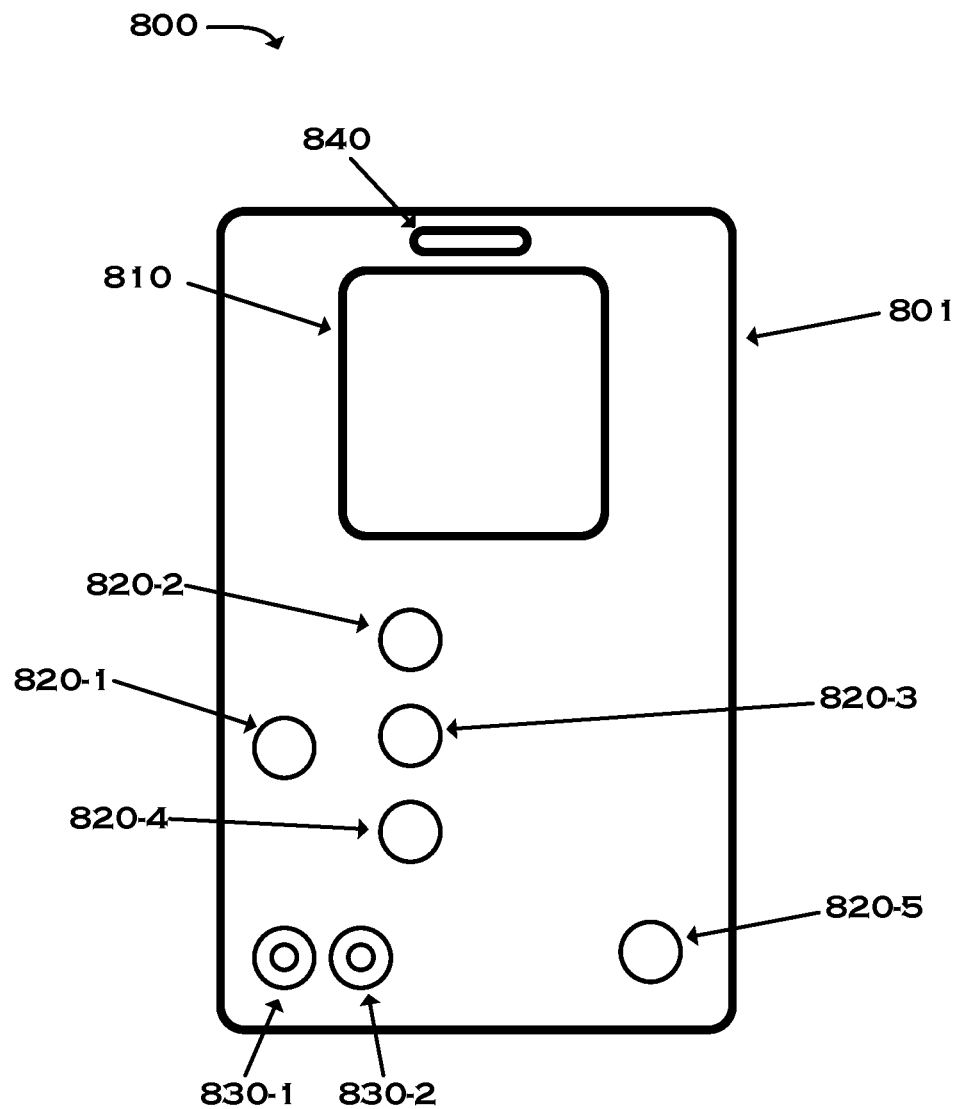
FIG. 8 illustrates a diagram of an example embodiment of a signal generator that may be used in connection with the systems, methods, technologies and/or techniques described herein.

FIG. 8 illustrates a diagram of a non-limiting example embodiment of a signal generator that may be used in connection with the systems and/or methods described herein. As shown in FIG. 8, signal generator 800 may include a housing 801, a display 810, one or more input devices 820 (e.g. as shown, 820-1, ... 820-N where N≥1, input devices are collectively referred to as "input devices 820"), signal connections 830-1 and 830-2, and speaker 840. Additionally, signal generator 800 may include the same and/or similar components to signal generator 120 and signal generator 320, such as those components described in relation to FIGS. 2 and 4. FIG. 8 depicts example components of signal generator 800, but in other implementations, signal generator 800 may include fewer components, additional components, different components or differently arranged components than illustrated in FIG. 8. For example, while input devices 820 are depicted as buttons, input devices may include any type of input device, including keyboards, keypads, joysticks, switches, dials, touchscreens, etc. In still other implementations, one or more components of the signal generator 800 may perform one or more tasks described as being performed by another one or more of the components of signal generator 800.

Housing 801 may include a chassis that mechanically secures and/or covers some or all of the components of signal generator 800. Speaker 840 may include a component to receive input electric signals from signal generator 800 and transmit audio output signals, which communicate audible information to a user of the signal generator 800.

Display 810 may include a component to receive electrical signal and present to the user a visual output in the form of text, images, video and/or a combination of text, images and videos, which visual output may communicate visual information to the user of the signal generator 800. In one implementation, display 810 may display text, images, videos and/or a combination of text, images and/or videos in response to inputs, such as via input devices 820 and/or inputs from signal connections 830. Additionally, or alternatively, display 810 may display text, images, videos and/or a combination of videos in response to signal generator 800 executing instructions (such a via a processor, like processing unit 420, etc.), including instructions based, in whole in or in part, on inputs received from input devices 820, signal connections 830, etc. The visual output may include information associated with the signal (e.g. signal presence, signal strength, signal level, etc.), the user (e.g. impedance of the user, etc.), information associated with using the signal generator (i.e. the signal generator is on, a distributor is connected, a circuit is closed, etc.), and/or other meditation content. Display 810 may be a touch screen that presents one or more images that correspond to control buttons. The one or more images may accept, as input, mechanical pressure from the user (e.g. when the user presses or touches an image corresponding to a control button or combinations of control buttons) and display 810 may send electrical signals to a processor, such as processing unit 420, that may cause signal generator 800 to transmit information, perform a function, etc.

Input devices 820 may include mechanisms that permit a user to input information to signal generator 800, such as keyboards, keypads, buttons, switches, etc. The arrangement of input devices 820 depicted in FIG. 8 is only one example arrangement of input device 820 or input devices 820 that may be included in signal generator 800. Input devices 800 may include one or more input mechanism that may permit a user to operate signal generator 800. As depicted in FIG. 8, input devices 820 may include an on button 820-1, used to activate/turn on the signal generator 800; a first mode button 820-2, used to select a first signal to be output by signal generator 800; a second mode button 820-3, used to select a second signal to be output by signal generator 800; a third mode button 820-4, used to select a third signal to be output by signal generator 800; and an off button 820-5, used to deactivate/turn off the signal generator 800. The first signal, second signal and third signal may be any of the signals described herein. In one embodiment, the signal generator 800 generates signals that correspond to a DC electrical signal (such as from about 2 volts to about 40 volts, preferably from about 9 volts to about 20 volts), and the first mode, second mode and third mode may correspond to different current levels, generally from about 0.1 milliamps to 5 milliamps. For instance, the first signal may correspond to a first current level of about 1 milliamp, the second signal may correspond to a second current level of about 1.5 milliamps, and the third signal may correspond to a third current level of about 2 milliamps. The current levels and voltage levels output by signal generator 800 may vary and may be determined by the needs of the user, the power source of signal generator, etc. Also, in other embodiments, signal generator 800 may output other signals, such as magnetic, AC power, etc.

Signal connections 830 may be receptacles, connections, quick disconnects, etc. via which signal generator 800 provides a signal. The embodiment of signal generator 800 depicted in FIG. 8 reflects two signal connections 830-1 and 830-2, but other embodiments of signal generator 800 may include additional signal connections 830 (such as in the event that signal generator is designed to provide a signal to multiple users) or a single signal connection. The signal connections 830-1 and 830-2 may correspond to connections for an electrical signal. For example, signal connection 830-1 may provide the signal to an electrode (i.e. an anode) that provides the signal to a user, such as anode 610. Signal connection 830-2 may correspond to a connection that receives the signal that has been applied to the user and received by an electrode (i.e. a cathode such as cathode 620) so that a circuit may be closed, allowing the signal to flow.

In addition to providing the signal, modifying the signal, and providing information associated with the signal, signal generator 800 may execute instructions to test the ability of signal generator 800 to provide a signal. For instance, and not limitation, signal generator 800 may conduct an impedance test which may provide a signal (which may be the signal to be provided to induce meditation, a low current, low voltage signal that is imperceptible to the user, etc.) to the user (i.e. via distributor) to test whether the circuit is closed or whether the resistance associated with the user may be too high to provide the signal. If the resistance is above a threshold, the signal generator may not provide the signal to the user. In one embodiment, the signal generator provides a relatively small current (e.g. 10 microamps, 100 microamps, etc.) to the distributor, and the signal generator measures the resistance associated with the user (e.g. across the circuit including the distributor with known resistance and the user) to determine the resistance, such as using Ohm's law. The maximum resistance may vary depending upon the signal to be delivered (e.g. electrical signal, other forms of signals, etc.), the strength of the signal to be applied (e.g. 5 volts, 20 volts, 40 volts, etc.), the placement of the distributor (the distance between the anode and cathode) and many other factors. In one embodiment, the threshold resistance for a 20 volt signal is within a range of 5,000 ohms to 20,000 ohms, more preferably 10,000 ohms (10k (2), such as when the distributor is positioned as shown in FIG. 7C. The threshold may vary widely for the reasons described herein.

Many other types of tests may be conducted by the signal generator 800, such as tests on the power level, ability to provide a signal, etc. The signal generator 800 may provide the signal only if the impedance test confirms an acceptable resistance associated with the user. If the impedance is above a threshold, the user may be prompted to lower resistance, such as by using a new/different distributor, cleaning the area of contact between the distributor and the user, etc. The impedance test may be conducted at any time, such as when the device is turned on, when one of the signal modes is selected, etc. Alternatively, the signal generator may constantly measure impedance and provide the signal only when the impedance is at an acceptable level.

Figure 9:
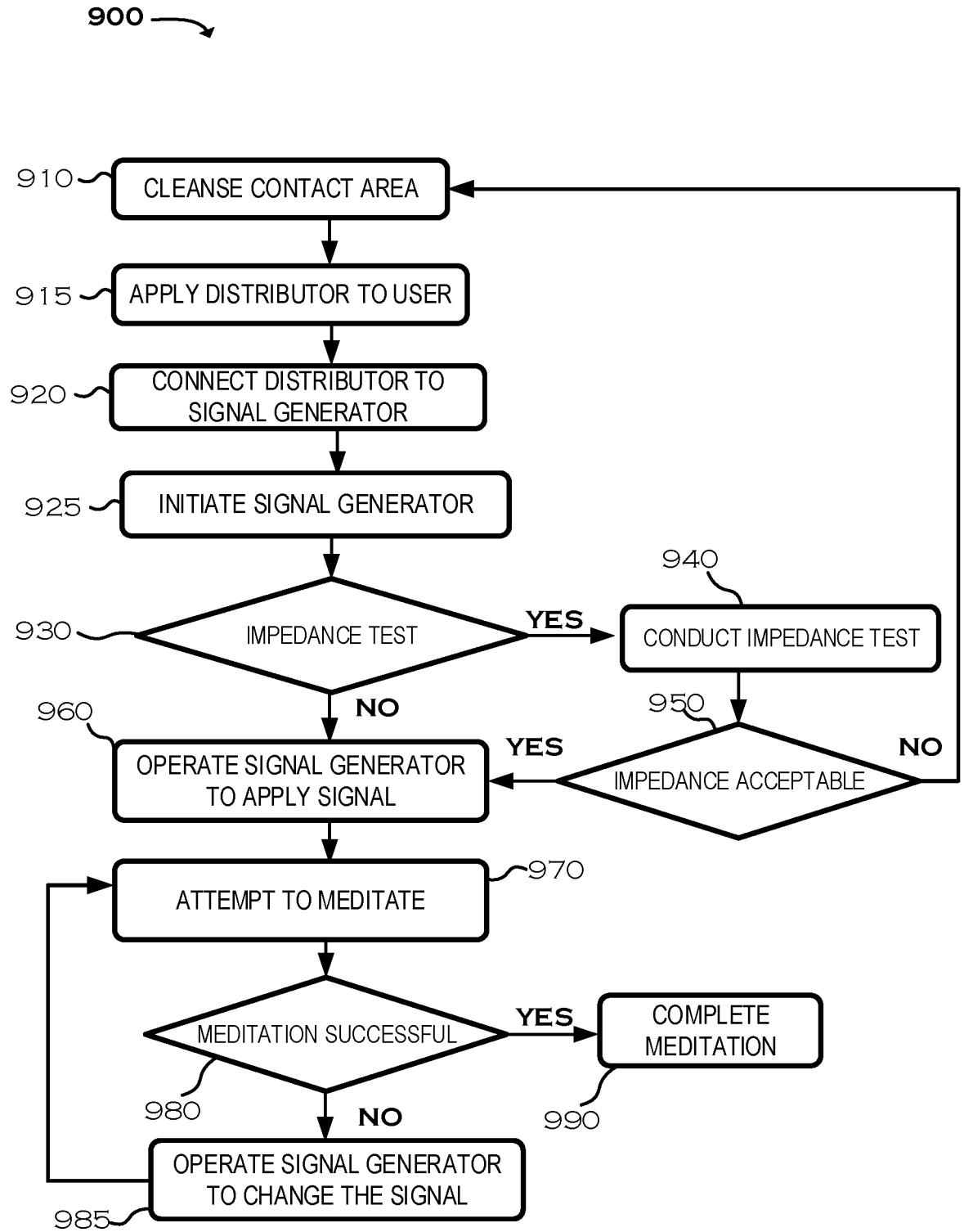
FIG. 9 is a flow chart of an example process that may be used to facilitate meditation using the systems, methods, technologies and/or techniques described herein.

FIG. 9 is a flow chart of an example process 900 that may be used to facilitate meditation using the systems, methods, technologies and/or techniques described herein. Process 900 may be performed using one or more of the devices associated with the meditation environments described herein. Additionally, or alternatively, some or all of process 900 may be performed using a device or collection of devices separate from, or in combination with, the devices associated with the meditation environments described herein. As shown in FIG. 9, process 900 may include cleansing a contact area (BLOCK 910), which may occur when a user uses a cleanser (e.g., alcohol, an astringent, soap, a facial cleanser, a wipe that contains a cleanser, etc.) and/or a wipe, paper towel, etc. to clean the area(s) of skin on which a distributor may be placed. Cleaning the contact area may lower the impedance associated with the user. The contact area of the user may be any of the areas associated with a brain portion described herein.

Process 900 may further include applying a distributor to the user (BLOCK 915) at the contact area. The distributor may include a single point of contact with the user, two points of contact (such as an anode and cathode), three points of contact with user, etc. The points of contact may be at or near the brain, auricular nerves, brain portion (e.g. the left and/or right frontal lobe, the left and/or right temporal lobe, the supplementary motor area or SMA regions of the brain (including Pre-SMA, SMA, posterior SMA, etc.) the left and/or right insula, the cingulate cortex (including posterior cingulate, PCC), and/or cranial nerves (including olfactory nerve, optic nerve, trigeminal nerve, facial nerve, glossopharyngeal nerve, vagus nerve (including auricular vagus nerve), hypoglossal nerve, auriculotemporal nerve, auricular nerves, etc.). The distributors may be placed on any surface of the body that may provide an input signal to the brain portion, including, but not limited to, the forehead, above the left and/or right eyebrow, the left and/or right temple, the supraorbital region, around the crown of the head (to engage the SMA and PCC regions of the brain), in or around the ears and/or other areas on or near the brain, auricular nerves, and/or cranial nerves, including areas having little and/or no hair.

Process 900 may further include connecting the distributor to the signal generator (BLOCK 920). Connecting the distributor to the signal generator may include using a connector, such as connector 130, that may transfer a signal from signal generator to distributor. Connector may include one or more wires or other conductive components that may permit the signal to be transferred along connector. Connector may also include electrical connectors (e.g. fittings, receptacles, etc.) that may be used to connect to distributor and/or signal generator. Alternatively, signal generator may be permanently connected to, or formed as a part of, distributor, which may eliminate the need to connect distributor to signal generator.

Process 900 may also include initiating the signal generator (BLOCK 925), which may include operating an input device (e.g. a button, a switch, a keypad, etc.) to turn on the signal generator and/or otherwise prepare the signal generator for operation. Initiating the signal generator may cause signal generator to conduct an impedance test (BLOCK 930-YES), which may cause the signal generator to run a test (BLOCK 940) to determine whether the impedance (i.e. resistant to electrical current flow, resistance to another type of signal, etc.) associated with a user is acceptable. Acceptable impedance may be, for instance, 5,000 ohms, 10,000 ohms, 20,000 ohms, etc. when the signal is an electrical signal and depending upon the particular signal to be applied and the placement of the distributor. The impedance test may include providing a low energy electrical current to the user via the distributors. The impedance test may further include determining the resistance is acceptable when the low energy electrical current is received by the signal generator after being applied to the user, which may confirm a closed circuit. When the lower energy electrical current is received by the signal generator, the impedance may be determined using, for instance, a multimeter or similar technology used to calculate electrical resistance, continuity, etc. The low level electrical current may not be perceptible by the user. The impedance test may be run before operating the signal generator to apply the signal (BLOCK 960). Additionally, or alternatively, the signal generator may constantly monitor impedance during use by, for instance, measuring impedance when applying the signal when the signal corresponds to an electrical power signal. In this embodiment, the signal may automatically shut off if the impedance level exceeds a threshold, which may occur when, for instance, the distributor accidentally comes off of the user, etc. The signal generator may notify the user (e.g. via a sound through a speaker, text and/or symbols on a display, etc.) that the impedance is acceptable or unacceptable, may provide the impedance of the user, etc. In some embodiments, the impedance of the user may decline once the signal has been applied for a period of time (e.g. one minute, two minutes, ten minutes, etc.).

If the impedance level is acceptable (BLOCK 950-YES) or if the signal generator does not conduct an impedance test (BLOCK 930-NO), the user may operate the signal generator to apply a signal (BLOCK 960). If the impedance level is not acceptable (BLOCK 950

NO), the user may attempt to reduce the impedance by, for instance, cleansing the area of contact between the user and the distributor (BLOCK 910). The user may repeat the steps described above as needed and conduct a second impedance test to determine whether the the impedance level associated with the user is acceptable. If the impedance level is acceptable, the user may operate the signal generator to apply a signal.

Operating the signal generator to apply the signal (BLOCK 960) may include any type of user input (e.g. via an input device) that may cause the signal generator to generate and output a signal to a distributor. For example, and not limitation, operating the signal generator to generate and apply the signal may include depressing a button, flipping a switch, etc. Operating the signal generator to apply the signal may be the same input by the user undertake to initiate the signal generator. For example, and not limitation, the user may initiate the signal generator, which may prompt the signal generator to conduct an impedance test and, upon passing the impedance test, the signal generator may begin applying the signal to the distributor(s).

Generating the signal may include, for instance producing the signal (e.g. via a battery, coil for magnets, etc.) and conditioning the signal, such as with a signal controller, to provide a signal at a particular strength, frequency, etc. Outputting the signal may include passing the signal directly to the distributor (e.g. via connection between signal generator and distributor) or passing the signal via a connector or series of connections through which the signal may be distributed to distributor and then to the user.

Once the signal is applied to the user, the user may attempt to meditate (BLOCK 970). Attempting to meditate may include, for instance, engaging in any of the practices and/or techniques used to enter a meditative state, such as sitting or lying comfortably, focusing on meditation, breathing calmly, listening to music, listening and/or watching meditation enhancing instructions/virtual reality content, etc. While meditating and/or attempting to meditate, the user may determine that the meditation is not successful and/or could be optimized (such as by reducing the signal to require the user to meditate with less assistance) (BLOCK 970-NO), which may cause the user to operate the signal generator to change the signal (BLOCK 985). Operating the signal generator to change the signal may including changing from a first signal (i.e. which results from BLOCK 960) to a second signal. The second signal may be stronger (i.e. have a higher amplitude, frequency, current level, etc.), which second signal may help the user engage in meditation when the user is having difficulty engaging in meditation. Additionally, or alternatively, the second signal may be associated with a lower strength than the first signal, such as when the first signal was too strong (i.e. uncomfortable and/or distracting) or when the user wants to meditate with less assistance from the signal generator (i.e. to move toward a goal of unassisted meditation). If the user determines that the second signal is appropriate for meditation, the user may continue to mediate. If the user determines that the second signal does not cause a successful meditation and/or the meditation could be optimized, the user may again operate the signal generator to change the signal from a second signal to a third signal.

The user may apply the signal (or adjust the signal or remove it in some as shown by BLOCK 985) and continue meditating until the meditation is successful (BLOCK 980-YES), at which point the user may complete the meditation (BLOCK 990). Completing the meditation may include removing the distributor, turning off the signal generator, etc.

The foregoing description provides illustration and description, but is not intended to be exhaustive or to limit the implementations to the precise form disclosed. Modifications and variations are possible in light of the above disclosure or may be acquired from practice of the embodiments. It will be apparent that the assemblies, systems, methods, technologies and/or techniques, as described above, may be implemented in many different forms of implementations described herein and illustrated in the figures. The actual or specialized components and/or materials used to implement the assemblies, systems, methods, technologies and/or techniques is not limited to the embodiments; it should be understood that components and/or materials may be designed to implement the assemblies, systems, methods, technologies and/or techniques based on the description herein.

It should be emphasized that the terms "comprises"/"comprising" when used in this specification are taken to specify the presence of stated features, integers, steps or components but does not preclude the presence or addition of one or more other features, integers, steps, components, or other groups thereof.

No element, act or instruction used in the present application should be construed as critical or essential to the embodiments unless explicitly described as such. Also, as used herein, the articles "a" and "an" are intended to include one or more items and may be used interchangeably with "one or more." Where only one item is intended, the term "one" or similar language is used. Further, the phrase "based on" is intended to mean "based, at least in part, on" unless explicitly stated otherwise.

While preferred embodiments of the invention have been shown and described, those skilled in the art will recognize that other changes and modifications may be made to the foregoing embodiments without departing from the scope and spirit of the invention. For example, specific shapes of various elements of the illustrated embodiments may be altered to suit particular applications. Additionally, the meditation system, and components thereof, may have different components or be designed in different shapes using different methods of connection without departing from the spirt of the invention disclosed herein. For example, and not limitation, the size and/or shape of distributor may be determined by the brain portion(s) the distributor is intended to target. Further, the embodiments disclosed herein may be used in different applications.

It is intended to claim all such changes and modifications as fall within the scope of the disclosure herein and the equivalents thereof.

What is claimed is:

1. A signal generator for providing a signal to a brain portion of a user to facilitate meditation, the signal generator comprising:
   a supply configured to provide an impedance signal and a further signal to the brain portion of the user,
   a processing unit that evaluates the impedance signal to test an impedance of the user by determining whether a resistance of the user exceeds a threshold, the processing unit configured to cause the signal generator to both:
      apply the further signal to the user when the resistance is at or below the threshold, and to
      not apply the further signal to the user when the resistance is above the threshold; and
   the further signal configured to be applied to the user while the user is engaging in meditation to assist the user in engaging in meditation; and
   a signal connection adapted for connection to a distributor, the distributor configured to apply the impedance signal and further signal to the brain portion of the user.

2. The signal generator of claim 1 further comprising a regulator connected to the supply, the regulator configured to adjust an output from the supply, the output configured to create the impedance signal or the further signal.

3. The signal generator of claim 1 further comprising an input device configured to control the further signal.

4. The signal generator of claim 1 where the impedance signal and the further signal correspond to an electrical signal.

5. The signal generator of claim 3 where the input device corresponds to a button configured to adjust the further signal.

6. The signal generator of claim 1, where each of the impedance signal and the further signal correspond to a direct current electrical signal having a current of from 0.1 milliamps to 5 milliamps.

7. The signal generator of claim 6 where the direct current electrical signal has a voltage of from 5 volts to 40 volts.

8. The signal generator of claim 1 where the signal connection includes a first signal connector configured to provide the impedance signal and the further signal to the distributor and a second signal connector configured to receive the impedance signal and the further signal from the distributor.

9. The signal generator of claim 1 where the processing unit executes instructions to test the impedance of the user.

10. The signal generator of claim 1 where the threshold is from 5,000 ohms to 20,000 ohms.

11. The signal generator of claim 1, where the impedance signal is weaker than the further signal and is imperceptible to the user.

12. The signal generator of claim 1 further including a display that provides a visual output to the user.

13. The signal generator of claim 1, where each of the impedance signal and the further signal correspond to a direct current electrical signal having a current of from 0.5 milliamps to 2 milliamps.

14. The signal generator of claim 1 further comprising a headband, the distributor and the signal generator being contained in the headband in an all-in-one arrangement.

* * * * *